US012151959B2

(12) United States Patent
Demirtas

(10) Patent No.: US 12,151,959 B2
(45) Date of Patent: Nov. 26, 2024

(54) METHODS OF ORGANIC WASTE STREAM CONVERSION

(71) Applicant: UCHICAGO ARGONNE, LLC, Chicago, IL (US)

(72) Inventor: Meltem Urgun Demirtas, Naperville, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 311 days.

(21) Appl. No.: 17/249,608

(22) Filed: Mar. 5, 2021

(65) Prior Publication Data

US 2021/0309549 A1 Oct. 7, 2021

Related U.S. Application Data

(60) Provisional application No. 62/985,853, filed on Mar. 5, 2020.

(51) Int. Cl.
| | |
|---|---|
| C12P 7/40 | (2006.01) |
| B01D 15/36 | (2006.01) |
| B01D 61/02 | (2006.01) |
| C02F 3/28 | (2023.01) |
| C02F 3/34 | (2023.01) |
| C02F 11/04 | (2006.01) |
| C12P 7/08 | (2006.01) |
| C12P 7/52 | (2006.01) |
| C12P 7/54 | (2006.01) |
| C12P 7/56 | (2006.01) |
| C02F 103/32 | (2006.01) |

(52) U.S. Cl.
CPC ............ *C02F 3/341* (2013.01); *B01D 15/363* (2013.01); *B01D 61/025* (2013.01); *B01D 61/027* (2013.01); *C02F 3/28* (2013.01); *C02F 11/04* (2013.01); *C12P 7/08* (2013.01); *C12P 7/40* (2013.01); *C12P 7/52* (2013.01); *C12P 7/54* (2013.01); *C12P 7/56* (2013.01); *B01D 2315/10* (2013.01); *C02F 2103/32* (2013.01); *C02F 2103/327* (2013.01)

(58) Field of Classification Search
CPC ....... Y02E 50/30; C12M 41/12; C12M 41/26; C12M 47/10; C12M 1/00; C02F 11/04; C02F 2103/32; C02F 3/28; C12P 7/6409; C12P 7/52; C12P 7/08; C12P 7/54; C12P 7/56; C12N 1/32
USPC ............................................... 435/136, 252.1
See application file for complete search history.

(56) References Cited

U.S. PATENT DOCUMENTS 6,797,140 B2 9/2004 Lin et al.

OTHER PUBLICATIONS

Domingos et al. ACS Sust. Chem. Eng. 2017, 5, pp. 1400-1407.*
Cheryan et al., Production of acetic acid by Clostridium thermoaceticum, Adv. Appl. Microbiol., 43:1-33 (1997), Abstract Only.
Coral et al., Batch fermentation model of propionic acid production by Propionibacterium acidipropionici in different carbon sources, Appl. Biochem. Biotechnol., 151(2-3):333-41 (Dec. 2008).
Ehsanipour et al., Fermentation of lignocellulosic sugars to acetic acid by Moorella thermoacetica, J. Ind. Microbiol. Biotechnol., 43(6):807-16 (2016).
Elferink et al., Anaerobic conversion of lactic acid to acetic acid and 1,2-propanediol by Lactobacillus buchneri, Appl. Environn. Microbiol., 67(1):125-32 (Jan. 2001).
Himmi et al., Propionic acid fermentation of glycerol and glucose by Propionibacterium acidipropionici and *Propionibacterium freudenreichii* ssp. *shermanii*, Appl. Microbiol. Biotechnol., 53(4):435-40 (Apr. 2000).
Santos et al., In situ product recovery techniques aiming to obtain biotechnological products: A glance to current knowledge, Biotechnol. Appl. Biochem., Online Only (Sep. 15, 2020).
Sim et al., Optimization of acetic acid production from synthesis gas by chemolithotrophic bacterium—Clostridium aceticum using statistical approach, Bioresour Technol., 99(8):2724-35 (May 2008).
Urgun-Demirtas et al., Waste to Bioproducts and Biofuels: Challenges and Opportunities in Driving Bioeconomy, Symposium on Biotechnology for Fuels and Chemicals (SBFC) organized by Society for Industrial Microbiology and Biotechnology, Seattle, Washington, Apr. 28-May 1, 2019, Abstract.
Urgun-Demirtas, Arrested Methanogenesis for Volatile Fatty Acid Production: Valorization of Industrial Wastewaters Beyond Biogas, at WEFTEC Conference, in a session dedicated on "Overview of the DOE's Integrated Efforts to Advance Resource Recovery and Energy Efficiency in the Nation's Water Systems", Sep. 29-Oct. 3, 2018.
Urgun-Demirtas, Bring It All Back to Nature: A New Paradigm in Environment-Energy-Nutrient Nexus, 2018 AIChE Midwest Regional Conference, Mar. 13-14, 2018, Chicago, Illinois, 34 pp.
Urgun-Demirtas, Dry Fermentation of Organic Wastes, at BETO and NREL Anaerobic Digestion Workshop, Apr. 24, 2018, Presentation.
Urgun-Demirtas, Ecosystem Services of Livestock Waste Based Energy Generation, ACES 2018 Conference, Dec. 3-6, 2018, Abstract and Presentation.
Urgun-Demirtas, New Perspectives for Biochar Utilization under Food-Water-Energy Nexus, 255th ACS National Meeting & Exposition, Mar. 18-22, 2018, New Orleans, Louisiana, Abstract and Presentation.
Duque, Anouk F., et al. "Response of a three-stage process for PHA production by mixed microbial cultures to feedstock shift: impact on polymer composition." New biotechnology 31.4 (2014): 276-288.

* cited by examiner

*Primary Examiner* — Robert B Mondesi
*Assistant Examiner* — Mohammad Y Meah
(74) *Attorney, Agent, or Firm* — MARSHALL, GERSTEIN & BORUN LLP

(57) ABSTRACT

Provided herein are methods of organic waste stream conversion including fermenting an organic waste stream with an inoculum using arrested methanogenesis to generate an organic product. The inoculum includes an anaerobic consortium isolated from cheese, yogurt, saline soil, kefir, and/or probiotics and the anaerobic consortium is pretreated to transform the anaerobic consortium into an acidogenic consortium.

19 Claims, 17 Drawing Sheets

METHODS OF ORGANIC WASTE STREAM CONVERSION

CROSS-REFERENCE TO RELATED APPLICATIONS

This application claims the benefit of the filing date of U.S. Provisional Application No. 62/985,853, filed Mar. 5, 2020, the disclosure of which is hereby incorporated by reference in its entirety.

STATEMENT REGARDING FEDERAL SPONSORED RESEARCH OR DEVELOPMENT

This invention was made with government support under grant number DE-AC02-06CH11357 awarded by the United States Department of Energy. The government has certain rights in the invention.

BACKGROUND

Field of the Disclosure

The disclosure generally relates to methods of organic waste stream conversion using arrested methanogenesis.

Brief Description of Related Technology

Anaerobic digestion (AD) is a process that breaks down organic material with the help of microorganisms in an environment where no oxygen is present. The end product of the AD process can be used for biofuel, bio-fertilizer, and electricity. However, the AD process can be stopped—or arrested—when an intermediate substrate is produced. For example, acetic acid is an intermediate substrate that is a highly valued metabolite and an important commodity to many industries for use in paint, polymers, resins, photographic films, and food flavoring. Current AD methods rely on energy and/or chemical intensive biogas treatment and upgrading operations.

Organic wastes generation continues to increase due to the global population increases. For example, production of 1 kg of cheese can create or generate 6 to 10 liters of wastewater, and the production of 1 liter of beer can create or generate 4 to 10 liters of wastewater. As these organic wastes increase, the development of new, renewable, and eco-friendly treatments for these organic wastes have been rising as well. One such example is dark fermentation, which produces hydrogen at low yields with short chain organic acid (SCOA) production as an intermediate product. These SCOAs can be used as preservatives in the food industry, building blocks in pharmaceutical companies, and used in perfume/fragrance industries. However, most attempts to produce hydrogen from organic waste via dark fermentation fall short of producing recoverable amounts of hydrogen due to accumulation of volatile fatty acids, digester community instability, and process upsets. Moreover, dark fermentation processes are challenged by feedstock cost, robustness and resiliency of microbes, and product titer and yield.

SUMMARY

In embodiments, a method of organic waste stream conversion can include fermenting an organic waste stream with an inoculum using arrested methanogenesis. The inoculum can be a regulated acidogenic metabolism inoculum. The fermenting can be performed with a sludge retention time and/or hydraulic retention time of no more than seven days at a pH of 7.5 or less to generate an organic product. The organic product can include one or more organic acids and/or alcohols. In embodiments, the inoculum can include an anaerobic consortium selectively isolated from one or more of cheese, yogurt, saline soil, kefir, and probiotics. The anaerobic consortium can be pretreated to transform the anaerobic consortium into an acidogenic consortium.

In embodiments, the method of organic waste stream conversion can further include separating the organic acids and/or alcohols from the organic product (fermenter effluent stream) to obtain an extracted product. The separation can be performed using ion-exchange resins, adsorbents, membrane filtration, electrodialysis, electrodeionization, or combinations thereof.

Further aspects and advantages of the disclosure will be apparent to those of ordinary skill in the art from a review of the following detailed description. While the compositions and methods are susceptible of embodiments in various forms, the description is illustrative and is not intended to limit the scope of the disclosure to the specific embodiments described herein.

DETAILED DESCRIPTION

Figure 1A:
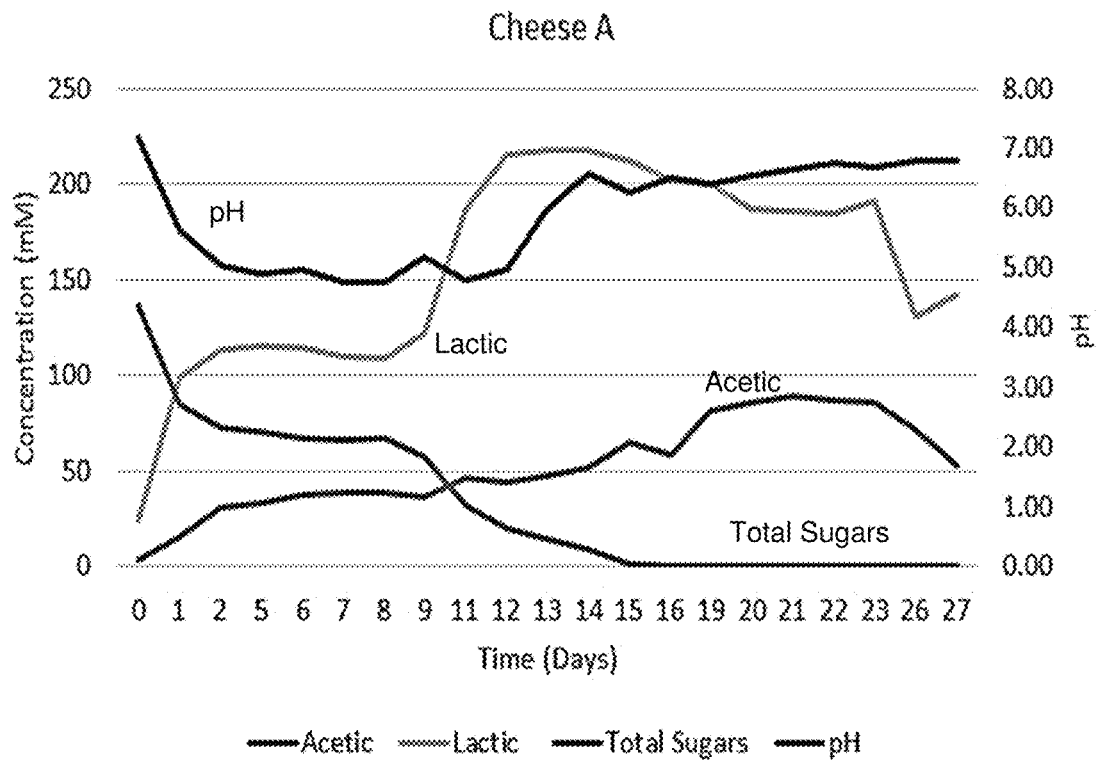
FIG. 1A is a graph showing the temporal changes in pH and concentrations of acetic acid, lactic acid, and total sugars in a cheese inoculum.

Disclosed herein are methods of converting organic waste streams, such as brewery wastewater, cheese whey wastewater, food waste, and other municipal and industrial organic wastes. The methods of the disclosure can utilize highly efficient, robust, and productive microbial community structures for the conversion process. These "microbial community structures" are referred to herein as "acidogenic consortia" (or an "acidogenic consortium") which can be prepared as described herein. Briefly, inocula including anaerobic consortia selectively isolated from cheese, yogurt, saline soil, kefir, and/or probiotics can be pretreated under various conditions to give the acidogenic consortia. The acidogenic consortia can be used to convert organic waste streams into useful organic acids and alcohols. Advantageously, the present inventors have found that the acidogenic consortia can transform organic waste streams into high value short chain organic acids (SCOAs). High value SCOAs typically having carbon chain lengths ranging from about 1 to about 6 carbon atoms, for example about 2 to about 6 carbon atoms. The methods of the disclosure can include the sustainable utilization of a rewired dark fermentation process to produce SCOAs and alcohols via arrested methanogenesis. The methods according to the disclosure can provide for the regulation of acidogenic metabolism toward enhanced, efficient, and robust SCOA production.

Significantly, the methods of the disclosure are flexible, such that the inoculum and various operating conditions (e.g., pH, temperature, duration, etc.) can be controlled to produce a targeted organic product, such as lactic acid, volatile fatty acids (VFAs), and/or ethanol. While conventional AD operations can be challenged by slow degradation rates, incomplete biodegradation, large footprints, and high capital and operating costs, the methods of the disclosure are advantageously cost-effective and adjustable to produce organic products under a number of various operating conditions.

In accordance with embodiments, the disclosure provides methods of organic waste stream conversion including fermenting an organic waste stream with an inoculum, which can be a regulated acidogenic metabolism inoculum, using arrested methanogenesis performed with a short sludge retention time and/or short hydraulic retention time at a pH of 7.5 or less to generate an organic product comprising one or more organic acids and/or alcohols. The inoculum includes an anaerobic consortium selectively isolated from cheese, yogurt, saline soil, kefir, and/or probiotics and pretreated to convert the anaerobic consortium or portion thereof to an acidogenic consortium. Advantageously, the inoculum can effectively ferment the organic waste stream to provide high concentrations of the desired products, such as SCOAs (e.g., lactic acid), while natural microorganisms and bacteria cannot. The efficacy of the inoculum is due in part to a pretreatment of the anaerobic consortia that transforms the anaerobic consortia into an acidogenic consortia, which can be used in the fermentation via arrested methanogenesis. For example, the pretreatment can selectively transform the anaerobic consortia into a specialized acidogenic consortia.

The methods of the disclosure can be effective in converting the organic wastes of a variety of organic waste streams or feedstocks. Examples of suitable organic waste streams that can be used in accordance with the methods include, but are not limited to, cheese whey wastewater, brewery wastewater, food waste, industrial organic waste, organic fraction of municipal solid waste, or any mixtures thereof. In embodiments, the organic waste stream includes cheese whey wastewater and/or brewery wastewater. For example, the organic waste stream can include about 2 parts cheese whey wastewater to about 1 part brewery wastewater, about 1 part cheese whey wastewater to about 1 part brewery wastewater, or about 1 part cheese whey wastewater to about 3 parts brewery wastewater. The methods can be carried out, for example, in anaerobic membrane bioreactors (AnMBRs).

As provided herein, the methods include an inoculum including an anaerobic consortium. The anaerobic consortium can have a significant biological diversity and syntrophic relations, which enable the integration of multiple fermentation pathways from different kinds of microorganisms. The anaerobic consortium can be selectively isolated from one or more of cheese, yogurt, saline soil, kefir, probiotics, and combinations thereof. In embodiments, the anaerobic consortium is isolated from cheese, such as cheese whey or parmiagiano reggiano. In embodiments, the anaerobic consortium is isolated from yogurt. In embodiments, the anaerobic consortium is isolated from saline soil, such as beach soil or other soil having a high salt content. In embodiments, the anaerobic consortium is isolated from kefir. In embodiments, the anaerobic consortium is isolated from probiotics. The inoculum can include a single anaerobic consortium (i.e., isolated from a single source), or the inoculum can include an anaerobic consortia (i.e., isolated from more than one source). For example, the inoculum can include a combination anaerobic consortia selectively isolated from at least two of cheese, yogurt, saline soil, kefir, and probiotics.

As provided herein, the anaerobic consortium is pretreated. The pretreatment conditions can be selected to regulate acidogenic metabolism towards sustainable organic acid production. In accordance with embodiments, pretreating the anaerobic consortium includes an acid shock treatment, a heat treatment, or a combination thereof.

The acid shock treatment can include subjecting the anaerobic consortium to a pH of about 4 or less, for example to a pH of about 1 to about 4. For example, the anaerobic consortium can be subjected to a pH of 4.0, 3.7, 3.5, 3.0, 2, 1.7, 1.5, 1.2, or 1.0. The acid shock treatment can be performed by treating the anaerobic consortium with a strong acid such as hydrochloric acid, nitric acid, sulfuric acid, hydrobromic acid, hydroiodic acid, perchloric acid, chloric acid, or a mixture thereof. The acid shock treatment can be performed by treating the anaerobic consortium with a weak acid such as phosphoric acid. In embodiments, the acid shock treatment can include treating the anaerobic consortium with each of a strong acid and a weak acid. In embodiments, the anaerobic consortium is pretreated with phosphoric acid, such as a 2N phosphoric acid. The acid shock treatment can be performed for about 2 hours to about 15 hours, for example at least about 2, 3, 4, 5, 6, 7, 8, or 9 hours and/or up to about 15, 14, 13, 12, 11, 10, 9, or 8 hours. For example, the acid shock treatment can be performed for about 2, 3, 4, 5, 6, 7, 8, 9, 10, 11, 12, 13, 14, or 15 hours. In embodiments, the acid shock treatment is performed for about 6 hours.

The heat treatment can include subjecting the anaerobic consortium to a high temperature, such as at least about 80° C. For example, the temperature can be in a range of about 80° C. to about 110° C. For example, the anaerobic consortium can be subjected to temperatures of at least about 80, 85, 90, 95, 100, 105, 110° C. and/or up to about 120, 115, 110, 105, or 100° C. For example, the anaerobic consortium can be subjected to temperatures of about 80° C., 85° C., 90° C., 95° C., 100° C., 105° C., 110° C., 115° C., or 120° C. In embodiments, the heat treatment is performed at a temperature of about 105° C. In embodiments, the heat treatment is performed at a temperature of about 80° C. to about 120° C. The heat treatment can be performed for at least about 2, 3, 4, 5, 6, 7, 8, or 9 hours and/or up to about 15, 14, 13, 12, 11, 10, 9, or 8 hours. For example, the heat treatment can be performed for about 2, 3, 4, 5, 6, 7, 8, 9, 10, 11, 12, 13, 14, or 15 hours. In embodiments, the heat treatment is performed for about 6 hours.

The pretreating of the anaerobic consortium can include both an acid shock treatment and a heat treatment. In embodiments wherein the pretreatment includes both acid shock and heat treatments, the acid shock and heat treatments can be performed in simultaneously, in overlapping manner, or sequentially (in either order). For example, the anaerobic consortium can be subjected to the acid shock treatment and the heat treatment, as described herein, at substantially the same time or with some portion of the processes overlapping in time. Alternatively, the anaerobic consortium can be subjected to the acid shock treatment followed by the heat treatment, or the anaerobic consortium can be subjected to the heat treatment followed by the acid shock treatment. When the pretreating includes both the acid shock treatment and the heat treatment, the pretreating can be performed for at least about 2, 3, 4, 5, 6, 7, 8, or 9 hours and/or up to about 15, 14, 13, 12, 11, 10, 9, or 8 hours. For example, the pretreating can be performed for about 2, 3, 4, 5, 6, 7, 8, 9, 10, 11, 12, 13, 14, or 15 hours.

The pretreating of the anaerobic consortium as described above (e.g., with an acid shock treatment and/or a heat treatment) can provide an acidogenic consortium. The acidogenic consortium can include a highly efficient, robust, and productive microbial community structures that are resilient to high salt and high carboxylate environments. Advantageously, the acidogenic consortium is more effective in the conversion of organic waste streams than the anaerobic consortium, which includes a natural microbial community structure. The acidogenic consortium provides an inoculum, e.g., a regulated acidogenic metabolism inoculum, which can be fermented with an organic waste stream in accordance with embodiments described herein.

The anaerobic and/or acidogenic consortium can include bacteria such as Actinomycetaceae, Bacillaceae, Clostridiaceae, Corynebacteriaceae, Enterococcaceae, Lactobacillaceae, Streptococcaceae, Moraxellaceae, and Paenibacillaceae. For example, the anaerobic and/or acidogenic consortia can include facultative anaerobes, such as those of the Bacillaceae, *Lactobacillus*, and *Bifidobacterium* family, which can survive in the presence and the absence of oxygen. Certain species of Bacillaceae are capable of breaking down complex carbohydrates, while other species can produce lactic acid. *Lactobacillus* includes facultative anaerobes and can be responsible for carboxylic acids production (lactic, formic, acetic acids, etc.). *Bifidobacterium* strains have been extensively used as probiotics in the food industry and have also been utilized to produce lactic acid and VFAs. The anaerobic and/or acidogenic consortia can include obligate anaerobes, such as those of the Clostridiaceae family, which can be oxygen sensitive. Various strains of Clostridiaceae can break down simple sugars into SCOAs such as acetic acid and butyric acid. In embodiments, the anaerobic and/or acidogenic consortium includes one or more bacteria selected from Bacillaceae, Clostridiaceae, Lactobacillaceae, Streptococcaceae, and Paenibacillaceae. The various bacteria and relative amounts thereof present in the anaerobic consortium (e.g., as natural bacteria isolated from cheese, yogurt, saline soil, kefir, probiotics, etc.) can differ from those present in the acidogenic consortium, for example, depending on the pretreatment. Similarly, the microbial community structure and dynamics thereof present in the acidogenic consortium can change over time as the fermentation with the organic waste stream occurs. Changes in bacterial concentration can also be observed during the fermentation process. For example, the acidogenic consortium can initially contain a particular amount of a bacteria, such as Paenibacillaceae, that during the course of fermentation decreases. Similarly, the acidogenic consortium can initially contain a particular amount of a bacteria, such as Enterococcaceae, that during the course of fermentation increases.

As provided herein, the methods of organic waste stream conversion include fermenting an organic waste stream with an inoculum, e.g., a regulated acidogenic metabolism inoculum using arrested methanogenesis. Methanogenesis is a natural process in anaerobic digestion in which microbial methanogens produce methane. The methods of the disclosure can stop, or arrest, this process, in order to produce highly valuable intermediate products. The methods of the disclosure utilize arrested methanogenesis be rewiring dark fermentation, a process commonly known in the art. Dark fermentation is commonly used to convert organic substances to hydrogen. However, through the use of the acidogenic consortia described herein, the fermentation of the disclosed methods can convert organic substances into highly valuable organic products, such as lactic acid and other organic acids and alcohols.

As provided herein, the organic waste stream can also be subjected to a pretreatment. In embodiments, the methods include pretreating the organic waste stream to wash out methanogens from the anaerobic consortia. Pretreating the organic waste stream to wash out (i.e., remove, minimize, etc.) the methanogens can increase the efficiency of the methods by more effectively arresting the process of methanogenesis. In embodiments, the organic waste stream is pretreated by aerating the organic waste stream with oxygen. The aeration of the organic waste stream can wash out methanogens from the consortia.

The fermentation of the disclosure can be performed with a sludge retention time and/or hydraulic retention time of no more than seven days. As known in the art, the SRT can be defined as the total mass of solids in the system per total mass of solids lost per day. As known in the art, the HRT can be determined, in part, by the volume and flow-rate of the system.

In embodiments, the sludge retention time can be 3 to 20 days. In embodiments, the sludge retention time is no more than 7 days, for example, at least about 0.5, 1, 2, 3, 4, or 5 days and/or up to about 7, 6.5, 6, 5, 4, or 3 days. In embodiments, the sludge retention time is about 5 days to about 7 days.

In embodiments, the hydraulic retention time can be 3 hours to 20 days, for example about 3 hours to 24 hours (1 day). Where the methods are continuously stirred in a reactor, the hydraulic retention time can be the same as the sludge retention time. For example, the hydraulic retention time can be 3 to 20 days. In embodiments, the hydraulic retention time is no more than 7 days, for example, at least about 0.5, 1, 2, 3, 4, or 5 days and/or up to about 7, 6.5, 6, 5, 4, or 3 days. In embodiments, the hydraulic retention time is about 5 days to about 7 days. In embodiments, the hydraulic retention time can be 3 to 24 hours. In embodiments, the hydraulic retention time can be 3 to 15 hours. In embodiments, the hydraulic retention time can be at least about 3, 4, 5, 6, 7, 8, 9, 10, 11, 12, 13, 14, or 15 hours and/or up to about 24, 23, 22, 21, 20, 19, 18, 17, 16, 15, 14, 13, 12, 11, 10, 9, 8, or 7 hours. In embodiments, the hydraulic retention time is about 3 hours to about 10 hours.

The fermentation of the disclosure can be performed at a pH of 7.5 or less, for example about 2 to about 7.5. In embodiments, the fermentation is performed at a pH of at least about 2, 2.5, 3, 3.5, 4, 4.5, or 5 and/or up to about 7.5, 7, 6.5, 6, 5.5, 5, or 4.5. In embodiments, the fermentation of the disclosure is performed at a pH of 6.0 or less. Advantageously, in some cases, when the fermentation is performed at a pH of 7.5 or less, e.g., at a pH of 6.0, the degradation of the complex sugars and organic waste in the organic waste stream can be more effective at producing short chain organic products, such as lactic acid, as opposed to fermentation at more acidic pH levels.

In embodiments, the pH must be maintained (e.g. constant) during fermentation through the addition of an alkaline solution due to continued surges of organic acid during the fermentation process. The alkaline solution can include one or more of calcium, magnesium, sodium hydroxide, potassium hydroxide, carbonates, and ammonium salts. In embodiments, the alkaline solution can be obtained from byproducts of the process, for example, from a downstream separation process performed by electrodeionization. The pH can be maintained, for example at a pH of 7.5 or less. For example, the pH can be maintained during fermentation at a pH of 6.0.

As described herein, the fermentation of the disclosure generates an organic product. In embodiments, the organic product flows from the fermenter as a fermenter effluent stream. The organic product can include one or more organic acids and/or alcohols. The particular identity of the organic acids and/or alcohols present in the organic product can depend on a number of factors, such as, for example, the temperature, pH, HRT, SRT, the waste stream, and inoculum used in the fermentation. Similarly, the relative amounts of the organic acids and/or alcohols present in the organic product can depend on a number of factors, such as, for example, the temperature, pH, HRT, SRT, the waste stream, and inoculum used in the fermentation. Examples of organic products that may be generated by the methods described herein include lactic acid, acetic acid, butyric acid, formic acid, propionic acid, valeric acid, isovaleric acid, and ethanol. Each of acetic acid, butyric acid, formic acid, propionic acid, valeric acid, and isovaleric acid can be referred to as volatile fatty acids (VFAs). In embodiments, the organic product includes a volatile fatty acid, such as acetic acid, butyric acid, formic acid, propionic acid, valeric acid, and isovaleric acid. In embodiments, the organic product includes ethanol.

In embodiments, the organic product includes lactic acid. In embodiments, the organic product includes at least about 10 g/L lactic acid. For example, the organic product can include at least about 10, 15, 20, 25, 30, 35, 40, 45, 50, 55, or 60 g/L. In embodiments, the organic product includes at least about 60 g/L lactic acid. The amount of lactic acid can alternatively, or additionally, be characterized by weight percent. In embodiments, the organic product includes at least about 7, 10, 15, 20, 25, 30, 35, 40, 45, or 50 wt % and/or up to about 95, 92, 90, 85, 80, 75, 70, 65, 60, 55, 50, or 45 wt % lactic acid, based on the total weight of the organic product.

In embodiments, the organic product includes butyric acid and acetic acid. In embodiments, the organic product includes at least about 10 g/L butyric acid and acetic acid. For example, the organic product can include at least at about 10, 12, 15, 17, 20, 22, 25, 30, 35, 40, or 45 g/L butyric acid and acetic acid. In embodiments, the organic product includes at least about 22 g/L butyric acid and acetic acid. The amounts of butyric acid and/or acetic acid can alternatively, or additionally, be characterized by weight percent. In embodiments, the organic product includes at least about 3, 5, 7, 10, 12, or 15 wt % and/or up to about 20, 17, 15, 13, 10, or 8 wt % acetic acid, based on the total weight of the organic product. In embodiments, the organic product includes at least about 3, 5, 7, 10, 15, 20, 25, 30 or 35 wt % and/or up to about 60, 57, 55, 52, 50, 45, 40, 35, 30 or 25 wt % butyric acid, based on the total weight of the organic product.

The organic product can further include one or more of formic acid, propionic acid, isobutyric acid, valeric acid, isovaleric acid, and ethanol. In embodiments, the organic product includes at least about 0.1, 0.2, 0.25, 0.30, 0.50, 0.75, 1.0, 2.0, or 3.0 wt % and/or up to about 5, 4.5, 4.0, 3.5, 3.0, 2.5, 2.0, or 1.5 wt % propionic acid, based on the total weight of the organic product. In embodiments, the organic product includes at least about 0.1, 0.2, 0.25, 0.30, 0.50, 0.75, 1.0, 2.0, or 3.0 wt % and/or up to about 5, 4.5, 4.0, 3.5, 3.0, 2.5, 2.0, or 1.5 wt % formic acid, based on the total weight of the organic product.

The fermentation of the disclosure can be performed at a temperature of about 20° C. to about 70° C., for example about 30° C. to about 70° C. For example, in embodiments, the fermenting is performed at a temperature of at least about 20, 25, 30, 35, 40, 45, 50, or 55° C. and/or up to about 70, 65, 60, 55, 50, 45, 40, or 35° C. The inventors advantageously found that the temperature of the fermentation can have an impact on the identity and relative amounts of organic acids and/or alcohols in the organic product. For example, it was found that fermentation at lower temperatures can result in higher relative amounts of lactic acid as compared to other organic acids and alcohols, whereas fermentation at higher temperatures can result in higher relative amounts of VFAs, such as butyric acid and acetic acid, as well as organic alcohols, such as ethanol. Without intending to be bound by theory, it is believed that at higher temperatures, the bacteria and microbes in the acidogenic consortia become stressed, which promotes the formation of alcohols via solventogenesis.

In embodiments, the fermenting is performed at a temperature of about 30° C. to about 40° C., for example at about 30, 31, 32, 33, 34, 35, 36, 37, 38, 39, or 40° C. Fermentation at this temperature can provide an organic product including lactic acid and other organic acids, such as acetic acid, butyric acid, and propionic acid, wherein the lactic acid is present in an amount greater than the other organic acids. For example, in embodiments, when the fermenting is performed at a temperature of about 30° C. to about 40° C., the organic product can include at least about 30, 40, 45, 50, 55, 60 or 65 wt % and/or up to about 95, 92, 90, 85, 80, 75, 70, 65, or 60 wt % lactic acid, based on the total weight of the organic product. Similarly, in embodiments, when the fermenting is performed at a temperature of about 30° C. to about 40° C., the organic product can include about 0.1 wt % to about 45 wt % of organic acids and alcohols, other than lactic acid.

In embodiments, the fermenting is performed at a temperature of about 45° C. to about 70° C., for example at about 45, 47, 50, 51, 52, 53, 54, 55, 56, 57, 58, 59, 60, 62, 65, 67, or 70° C. Fermentation at this temperature can provide an organic product including volatile fatty acids, such as butyric acid and acetic acid, as well as other organic acids such as formic acid and propionic acid, wherein the butyric acid and acetic acid are present in amounts greater than the other organic acids. Fermentation at this temperature can provide an organic product further including ethanol. For example, in embodiments, when the fermenting is performed at a temperature of about 45° C. to about 70° C., the organic product can include at least about 10, 15, 20, 25, 30, 35, 40, 45, or 50 wt % and/or up to about 80, 75, 70, 65, 60, 55, 50, 45, 40, or 35 wt % butyric acid and acetic acid, based on the total weight of the organic product. Similarly, in embodiments, when the fermenting is performed at a temperature of about 45° C. to about 70° C., the organic product can include about 5 wt % to about 20 wt % ethanol, based on the total weight of the organic product.

The methods of the disclosure can further include separating the organic acids and/or alcohols from the organic product (fermenter effluent stream) to provide an extracted product. The extracted product can advantageously have a high concentration of the desired organic products (e.g., lactic acid), as well as high purity.

The extracted product can include increased amounts of lactic acid, relative to the organic product. For example, the extracted product can include at least about 20, 22, 25, 27, 30, or 32 wt % and/or up to about 40, 37, 35, 32, 27, or 25 wt % lactic acid. In embodiments, the extracted product includes from about 20 wt % to about 40 wt % lactic acid. The extracted product can include increased amounts of butyric acid, relative to the organic product. For example, the extracted product can include at least about 20, 22, 25, 27, 30, or 32 wt % and/or up to about 40, 37, 35, 32, 27, or 25 wt % butyric acid. In embodiments, the extracted product includes from about 20 wt % to about 40 wt % butyric acid.

The organic acids and/or alcohols can be separated from the organic product using ion-exchange resins, adsorbents, membrane filtration, electrodialysis, electrodeionization, or any combination thereof.

Examples of suitable ion-exchange resins include AMBERLITE® IRN-78, AMBERLITE® IRN-67, DIAION® WA-10, AMBERLITE® FPA66 (formerly DOWEX® 66), and AMBERLYST® A26. In embodiments, the ion-exchange resin includes AMBERLITE® IRN-78. This resin, IRN-78, is a strong base resin including a styrene divinylbenzene copolymer matrix with trimethyl ammonium functional groups. It has a total exchange capacity of at least about 1.20 eq/L, a moisture content of about 54% to about 60%, and a density of about 690 g/L. In embodiments, the ion-exchange resin includes AMBERLITE® IRA-67. This resin, IRA-67, is a weak base resin including a crosslinked acrylic gel matrix with tertiary amine functional groups. It has a total exchange capacity of at least about 1.60 eq/L, a moisture content of about 56% to about 64%, and a density of about 700 g/L. The ion-exchange resin can be used in an amount of about 0.5 g to about 50 g, for example, about 0.5, 0.6, 0.7, 0.8, 0.9, 1.0, 1.5, 2.0, 2.5, 3.0, 4.0, 5.0, 6.0, 7.0, 8.0, 9.0, 10.0, 15, 20, 25, 30, 35, 40, 45, or 50 g, based on the wet mass of the resin. For example, the ion-exchange resin can be used in an amount of at least about 0.5, 1.0, 2.0, 4.0, 10, or 20 g and/or up to about 50, 45, 40, 35, 30, 25, 20, 25, or 10 g, based on the wet mass of the resin. In embodiments, where the organic product has a pH of about 8 or less, the ion-exchange resin can include AMBERLITE® IRA-67. In embodiments, where the organic product has a pH of at least about 7.5, the ion-exchange resin can include AMBERLITE® IRN-78.

The ion-exchange resin can recover at least about 5 wt % of the acid, e.g., acetic acid, present in the organic product. For example, the ion-exchange resin can recover at least about 5, 10, 20, or 30 wt % and/or up to about 60, 55, 50, 45, 40, or 30 wt % of the acid present in the organic product.

Examples of suitable membrane filtration methods that can be used include, for example, ultra-filtration, nanofiltration, and reverse osmosis.

Ultra-filtration can utilize a membrane having a polyethersulfone and a pore size suitable for compounds having molecular weights of about 10,000 Da. Ultrafiltration can be used most efficiently with relatively pure organic product feeds. Ultrafiltration can be carried out at a pH of as low as about 1 and as high as about 11.

Nanofiltration can utilize a membrane having a polyamide-TEC and a pore size suitable for compounds having molecular weights of about 200 Da to about 400 Da. Nanofiltration can be used with a variety of organic product feeds, such as surface water or groundwater, industrial or commercial water, and food and beverage wastewater (e.g., cheese whey wastewater, brewery wastewater, etc.). Nanofiltration can be carried out at a pH of as low as about 2 and as high as about 11.

Reverse osmosis can utilize a membrane having a polyamide-TEC and a pore size suitable for compounds having molecular weights of about 100 Da. Reverse osmosis can be used with organic product feeds including seawater or brackish water. Reverse osmosis can be carried out at a pH of as low as about 2 and as high as about 12.

Figure 15:
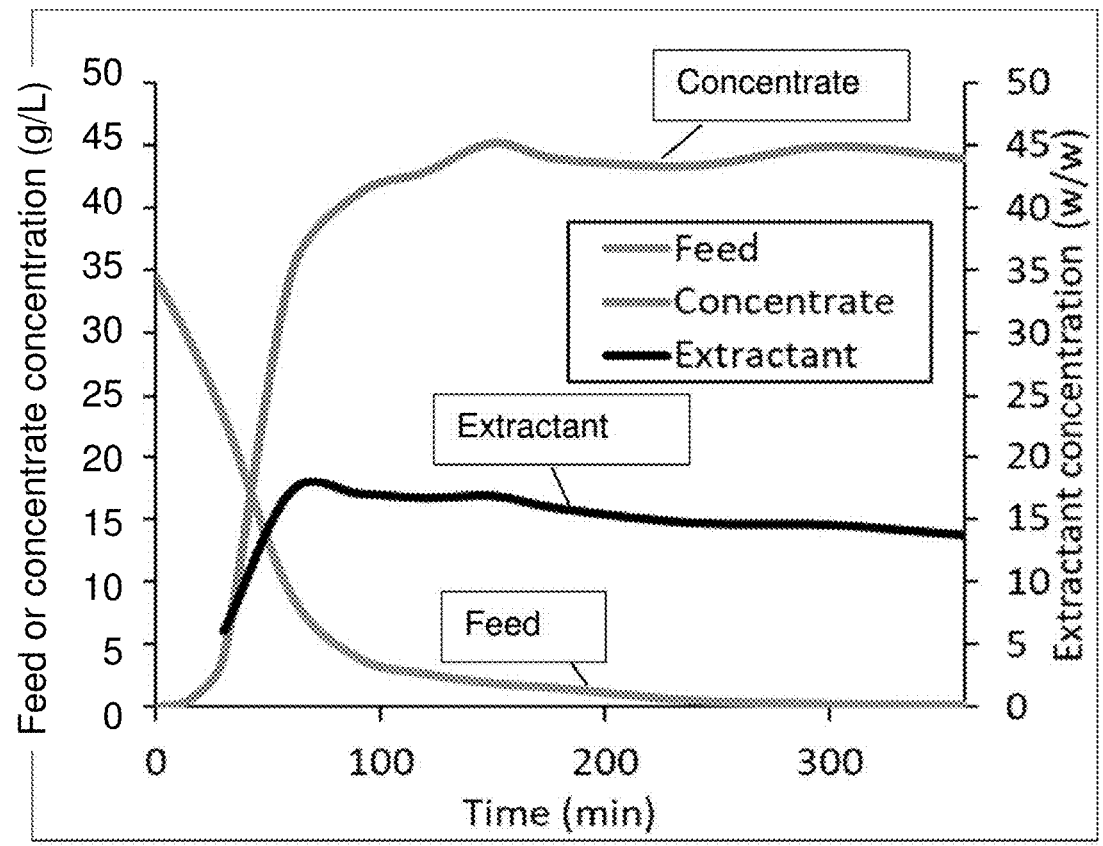
FIG. 15 is a graph showing organic acid concentration in the fermenter environment and after electrodeionization (EDI) process for a method in accordance with embodiments of the disclosure.

In embodiments, electrodeionization (EDI) is performed as described in U.S. Pat. No. 6,797,140, the disclosure of which is incorporated herein by reference. Referring to FIG. 15, elecrodeioonization separation was found to result in a more than 2× increase in organic acid concentration. In particular, in the embodiment illustrated in FIG. 15, the organic acid concentration of the fermentation product was 35 g/l, which increased to a concentration of 136.4 g/l in the product resulting from the EDI process.

In embodiments, the electrodeionization separation method results in an alkaline solution by-product, which can be recycled into the process, for example, for maintaining a stable pH during fermentation. Recycling of the alkaline stream from the EDI unit back to the fermenter for pH control can advantageously reduce the cost of the process.

The separation can be performed at any suitable pH for the particular separation method used. For example, the separation can be performed with an ion-exchange resin at a pH of about 3.5 to 14, for example at least about 3.5, 4, 4.5, 6, 7, or 8 and/or up to about 14, 12, 11, 19, 8, or 7. When using an ion-exchange resin, the particular pH can be selected based on the particular ion-exchange resin.

It is understood that while the disclosure is read in conjunction with the detailed description thereof, the foregoing description and following examples are intended to illustrate and not limit the scope of the disclosure, which is defined by the scope of the appended claims. Other aspects, advantages, and modifications are within the scope of the following claims.

EXAMPLES

Example 1—Preparation and Evaluation of Microbial Inocula

Six different inocula were studied: soil from a beach in New Orleans, LA, food waste, yogurt probiotics, kefir, a mixed culture of soil and food waste from a prior experiment, *Clostradium aceticum* inoculum from a prior experiment, and a 20-month Parmigiano Reggiano from Trader Joe's.

Four of the inocula were subjected to an acid shock pretreatment: (1) soil from a beach in New Orleans, (2) yogurt probiotics, (3) kefir, and (4) 20 month Parmigiano Reggiano from Trader Joe's. Specifically, these inocula were exposed to acid-shock treatment for 6 hours at a pH of 3 by using 2N phosphoric acid. Following the acid-shock treatment, each inoculum was purged with He gas at 70° C.

Before adding the inocula to the reactors, as described below, the pH was adjusted to 6.0 with 2N NaOH. The bottles were kept in an incubated shaker with a temperature of 40-55° C. and a shaking rate of 150 rpm.

Arrested Anaerobic Digester Operation and Enrichment Framework

The digester experiments were conducted in 500 mL glass serum bottles with a working volume of either 300 mL or 150 mL. Each bottle contained an autoclaved nutrient media (10 g/L sucrose, 5 g/L yeast extract, 7 g/L $K_2HPO_4$, 7 g/L $NaHCO_3$, 0.5 g/L $NH_4Cl$, 1 ml/L nutrient mix and 1.37 ml/L vitamin mix), either 25 g/L or 50 g/L cheese whey (a dairy industry food waste) and an inoculum, as provided above, in an amount of 10 vol % of sample volume. The bottles were then purged with helium for three minutes to establish an anaerobic environment, and wrapped in foil to block light to simulate dark fermentation. The bottles were kept in an incubated shaker at 55° C. with an rpm of 150.

Each day, 5 ml of the sample (i.e., the "fermenter sample") was collected for pH and HPLC analysis. The pH of each sample was measured and the digesters adjusted to a pH of 6.0 with 2N NaOH and/or 2N HCl.

The tested samples are identified as follows:
(A-I) New Orleans saline soil sample+sucrose, vitamin mixture and food waste mixture+digester containing 50 g/L cheese whey.
(A-II) New Orleans saline soil sample+sucrose, vitamin mixture and food waste mixture+digester containing 50 g/L cheese whey.
(B-I) New Orleans saline soil sample+sucrose, vitamin mixture and food waste mixture, pH controlled+digester containing 50 g/L cheese whey+lactic acid spike.
(B-II) New Orleans saline soil sample+sucrose, vitamin mixture and food waste mixture, pH controlled+digester containing 50 g/L cheese whey+lactic acid spike.
(C-I) New Orleans saline soil sample+sucrose, vitamin mixture and food waste mixture, pH controlled+digester containing 50 g/L cheese whey
(C-II) New Orleans saline soil sample+sucrose, vitamin mixture and food waste mixture, pH controlled+digester containing 50 g/L cheese whey
(D-I) New Orleans saline soil, yogurt probiotics and kefir culture+digester containing 50 g/L cheese whey
(D-II) New Orleans saline soil, yogurt probiotics and kefir culture+digester containing 50 g/L cheese whey
(X-I) New Orleans saline soil, *C. aceticum, C. formicaceticum*, yogurt probiotics and kefir culture+digester containing 25 g/L cheese whey
(X-II) New Orleans saline soil, *C. aceticum, C. formicaceticum*, yogurt probiotics and kefir culture+digester containing 50 g/L cheese whey
(Cheese A) 20-month Parmigiano Reggiano from Trader Joe's+digester containing 25 g/L cheese whey
(Cheese B) 20-month Parmigiano Reggiano from Trader Joe's+digester containing 25 g/L cheese whey
(Kefir A) Kefir+digester containing 25 g/L cheese whey
(Kefir B) Kefir+digester containing 25 g/L cheese whey DNA Extraction and High-Throughput 16S rRNA Sequencing Each fermenter sample that was collected throughout the various operational phases were stored at −80° C. until DNA extraction. A 1 mL aliquot of each fermenter sample was used for DNA extraction using the Powerlyzer® PowerSoil® DNA Isolation Kit (MO BIO Laboratories Inc., Carlsbad, CA) according to the manufacturer's instructions. The concentration of extracted DNA was determined using the NanoDrop ND-2000 spectrophotometer (NanoDrop, Wilmington, DE).

The microbial community structure was characterized using the high-throughput sequencing of PCR amplicons. In brief, PCR amplicon libraries were obtained using a primer set adapted from the Illumina HiSeq2000 and MiSeq. Specifically, primers (515F-806R) targeting the V4 region of the 16S rRNA gene were used for amplification. The forward amplification primer also contained a twelve-base barcode sequence that supported pooling of up to 2167 different samples in each lane. Operational taxonomic unit (OTU) tables and summaries were generated by using the QIIME (v1.8). Representative sequences of the OTU were aligned against the Greengenes 13_8 reference (97% PyNAST alignment template).

HPLC Sample Preparation and Analysis

Samples for HPLC analysis were diluted and filtered with a 0.45 μm and a 0.22 μm filter before being analyzed on the HPLC. Samples were run on an Agilent Technologies 1260 Infinity II HPLC with a Hi-Plex H Guard column (50×7.7 mm) and Hi-Plex H column (300×7.7 mm). HPLC operating conditions were as follows: 14 mM sulfuric acid mobile phase, 30 μL sample volume, 0.4 ml/min flow rate, 40° C. temperature, maximum pressure of 38 bar, and VWD wavelength of 210 nm.

Results

Figure 1B:
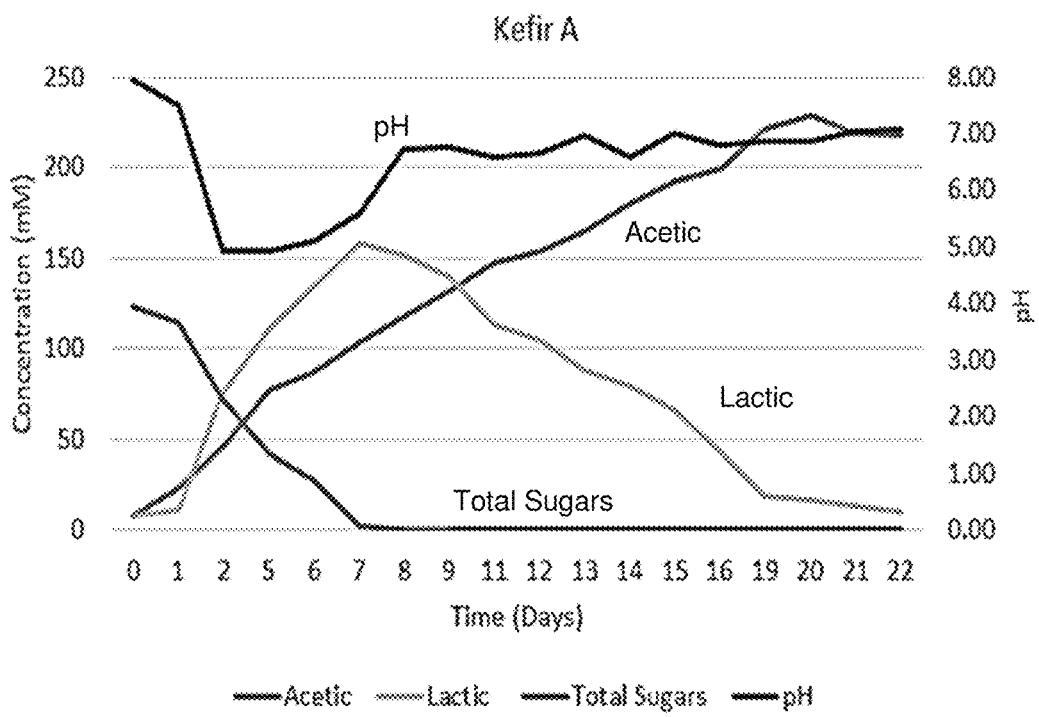
FIG. 1B is a graph showing the temporal changes in pH and concentrations of acetic acid, lactic acid, and total sugars in a kefir inoculum.

The results demonstrated that within the cheese and kefir bioreactors, the pH dropped significantly in the first few days as sugars were fermented into short-chain fatty acids (FIGS. 1A and 1B).

The target pH for the cheese containing culture medium was initially 4.5, which resulted in no pH adjustment for 9 days. Between the third and the ninth day total sugars slightly decreased and there was no increase in lactic acid. On the ninth day, the pH was adjusted to be closer to 7, and 2N NaOH was added to the bioreactor every day until the pH recovered. It took Cheese A 13 days to be at a pH over 6, and Cheese B 16 days. Total sugar concentration did not decrease to undetectable levels until the 19th day of the experiment (FIG. 1A).

The pH of kefir was adjusted immediately towards higher pH values around 6.5, and the kefir bioreactors did not remain at a pH under 6 for longer than four days (FIG. 1B). In the kefir sample, sugar degradation progressed very quickly and within seven days total sugar concentrations had dropped to undetectable levels. During this time lactic acid concentration increased sharply and peaked around day 7 (FIG. 1B).

Figure 2A:
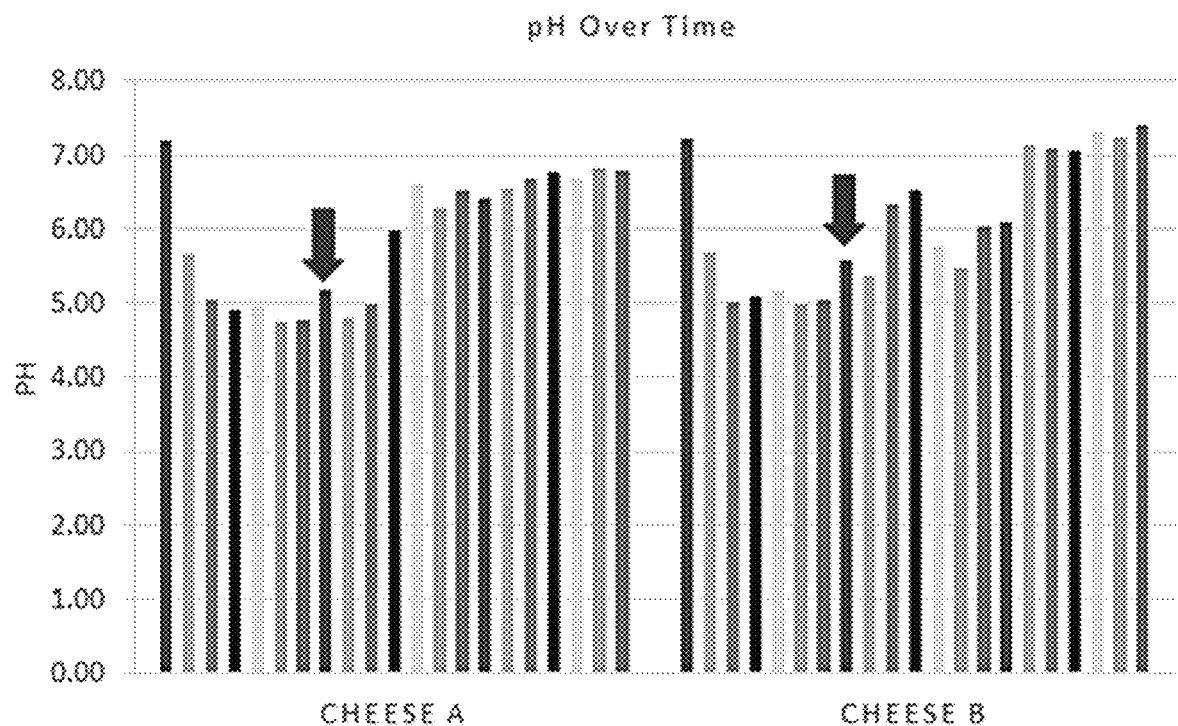
FIG. 2A is a graph of the temporal changes in pH of two cheese inocula.
Figure 2B:
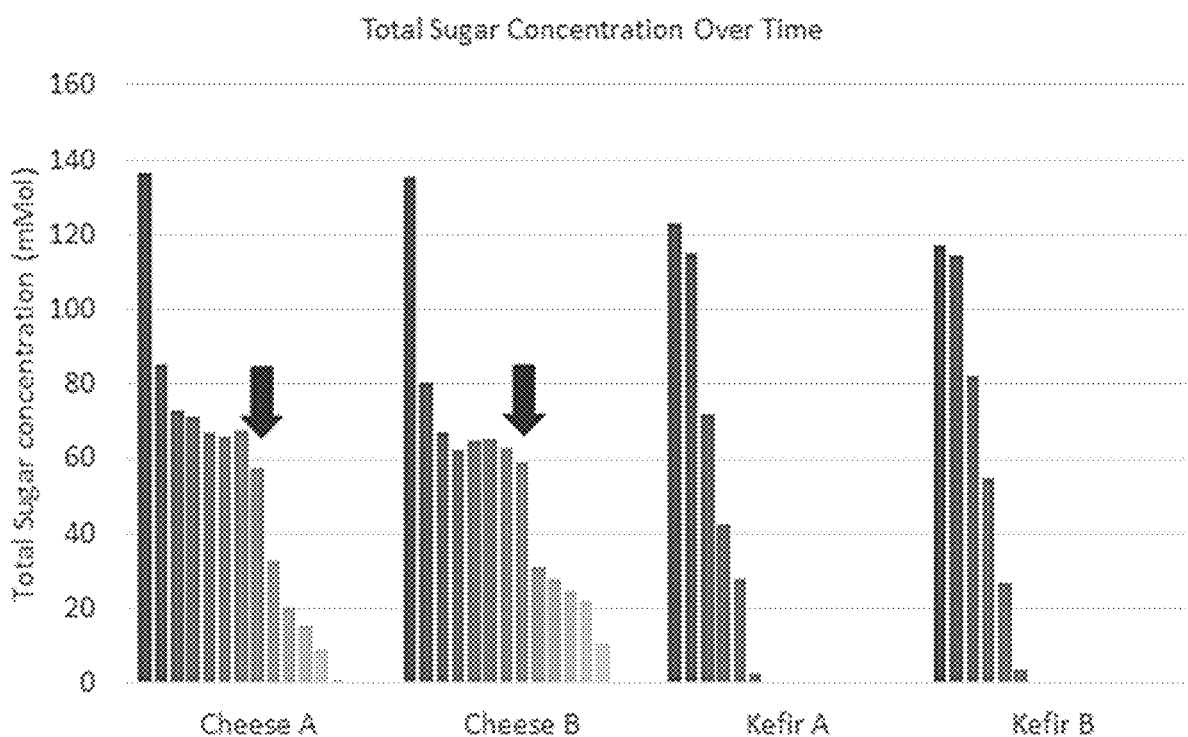
FIG. 2B is a graph of the temporal changes in total sugar concentration of two cheese inocula and two kefir inocula.

These data suggested that for the cheese and kefir samples studied, a neutral pH was more conducive to sugar degradation and lactic acid production than a low pH of less than 5.0. A correlation was observed between the beginning of pH adjustment in cheese samples and the uptick of sugar degradation to lactic acid (FIGS. 2A and 2B, where the arrow indicates beginning of pH adjustment).

Lactic acid production in New Orleans soil samples (X-I and X-II) did not hit a plateau-like in the cheese samples, yet similar to cheese, the soil samples were not pH adjusted and were therefore at a pH of 5 or lower. Despite this, lactic acid production proceeded similarly to adjusted samples, increasing sharply until reaching its peak several days into the experiment. The two samples at low pH during the initial phase did not behave in the same manner, suggesting the microbes in X samples were better equipped for sugar degradation and lactic acid production at low pH than those of cheese. Without intending to be bound by theory, this is believed to be because X samples were a mixed inoculum isolated from beach soil, which made it more robust and resilient.

Figure 3:
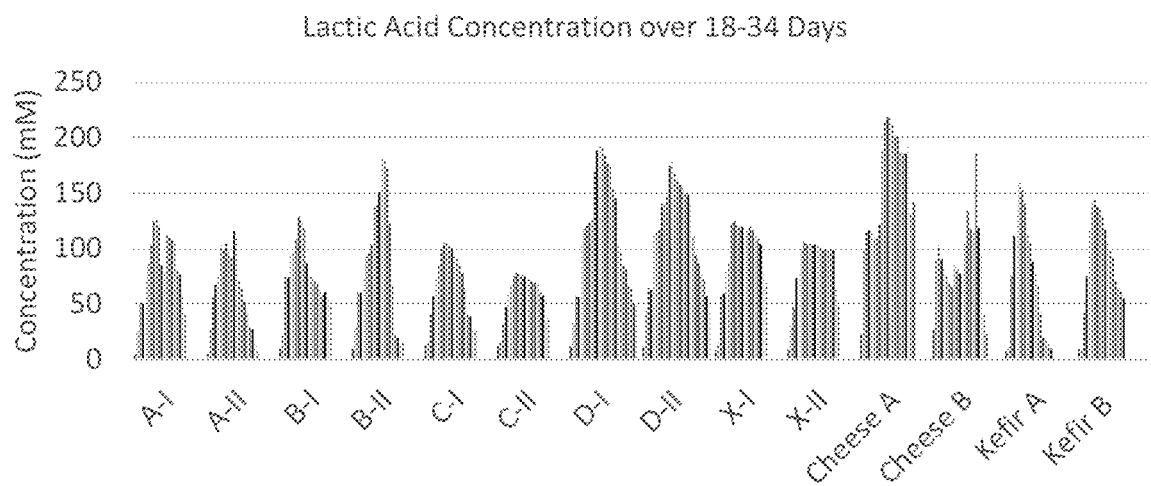
FIG. 3 is a graph of the temporal lactic acid production of fourteen inocula.

As shown in FIG. 3, the samples that produced high amounts of lactic acid were B-II at 181.6 mM, D-I at 194.4 mM, D-II at 179.4 mM, Kefir A at 158.8 mM, Kefir B at 143.0 mM and Cheese A at 218.2 mM (FIG. 3). The results showed that lactic acid production is tied to the concentration of cheese whey added into the fermenter. For example, the samples that produced high amounts of lactic acid included samples B-II, D-I, and D-II, which all started with 50 g/L cheese whey. It should also be noted that cheese A (which produced the highest amount of lactic acid), and kefir samples started with only 25 g/L cheese whey had higher lactic acid production as well. Each of the cheese and kefir samples likely also contained lactose, so the actual lactose availability may have been higher than just that which was present in the 25 g/L cheese whey.

Figure 4:
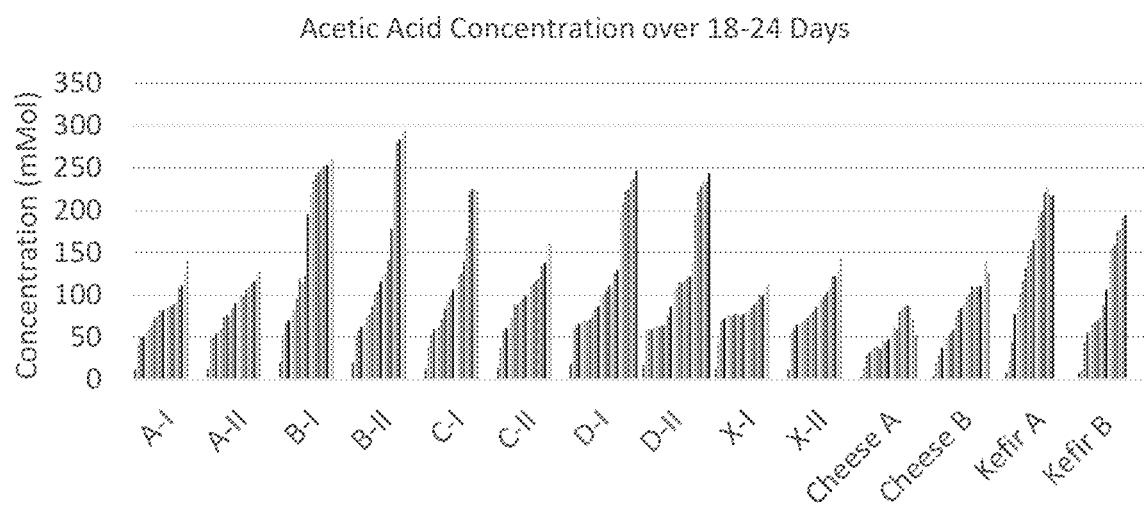
FIG. 4 is a graph of the temporal acetic acid production of fourteen inocula.

Generally, the samples that produced the highest amounts of lactic acid also produced the highest amounts of acetic acid (FIG. 4). Samples B-II, D-I, D-II, and Kefir all produced the highest amounts of acetic acid, the highest being 293.4 mM by B-II. These samples all produced higher concentrations of acetic acid than lactic acid, suggesting that acetic acid was not only due to degradation of lactic acid but also produced directly during sugar degradation. The exception to this trend was the cheese samples. The cheese samples produced a very high concentration of lactic acid but at the time the experiment was terminated had converted very little of it to acetic acid. Cheese A produced a higher amount of lactic acid, yet cheese B produced a higher amount of acetic acid at 139.8 mM. In other samples, lactic acid had been mostly degraded at the end of the experiment, whereas in cheese A over 140 mM remained.

All samples that were adjusted towards a neutral pH for the entire experiment showed an acetic acid concentration at least 1.1 times, and up to 2 times, the lactic acid concentration. The only two samples that showed an acetic acid concentration less than 1 time greater were X-I and cheese A, with concentrations of 0.9 times and 0.4 times that of lactic acid, respectively. It is believed that this could be due to low pH conditions. Many bacteria are known to be sensitive to acetic acid in its protonated/non-dissociated form because it travels freely across the cell membrane and reduces internal pH, thereby making the cytoplasm more acidic. At a pH of 4.75, which is the pKa of acetic acid, half the acid would be non-dissociated. When pH decreases from neutral and descends closer to the pKa value, the proportion of the non-dissociated acid would increase. Therefore, since the pH of the cheese bioreactors stayed under 6 for so long, the proportion of non-dissociated acetic acid would have been greater than at neutral and would have had a long time to affect the bacteria within the environment. By the time the environment within the cheese bioreactor was changed to a more hospitable pH, the proportion of acetic acid bacteria within the community had decreased enough to render the sample inefficient at producing acetic acid compared to samples that were kept neutral. The same is true of sample X-I. Each of the X samples also produced lactic acid concentrations similar to other samples with the starting 25 g/L cheese whey, yet produced less acetic acid. The fact that both non-pH adjusted samples had low lactic acid to acetic acid conversion rates suggested that low pH hinders acetic acid producers more heavily than other bacteria.

Example 2—Bench-Scale Batch Fermentation

Serum bottle experiments were conducted in 0.5 L glass bottles, with a 0.4 L working volume. The fermentation was run at a temperature of 55° C. and a cheese whey powder (CW) solution with brewery wastewater (BWW) as the feed. Brewery wastewater is generated in large quantity during the beer brewing process, and cheese whey is a waste stream generated during the production of cheese. The solutions were buffered using NaOH/HCl to a target pH of 6. The inoculum tested were mixed cultures originally from New Orleans Beach saline soil. Each sample was tested in duplicate and the following variation of CW concentration in the BWW was used:

| | Group | | |
|---|---|---|---|
| | BC-I | BC-II | BC-III |
| CW Concentration (g/L) | 13.75 | 38.12 | 50.00 |

Figure 5:
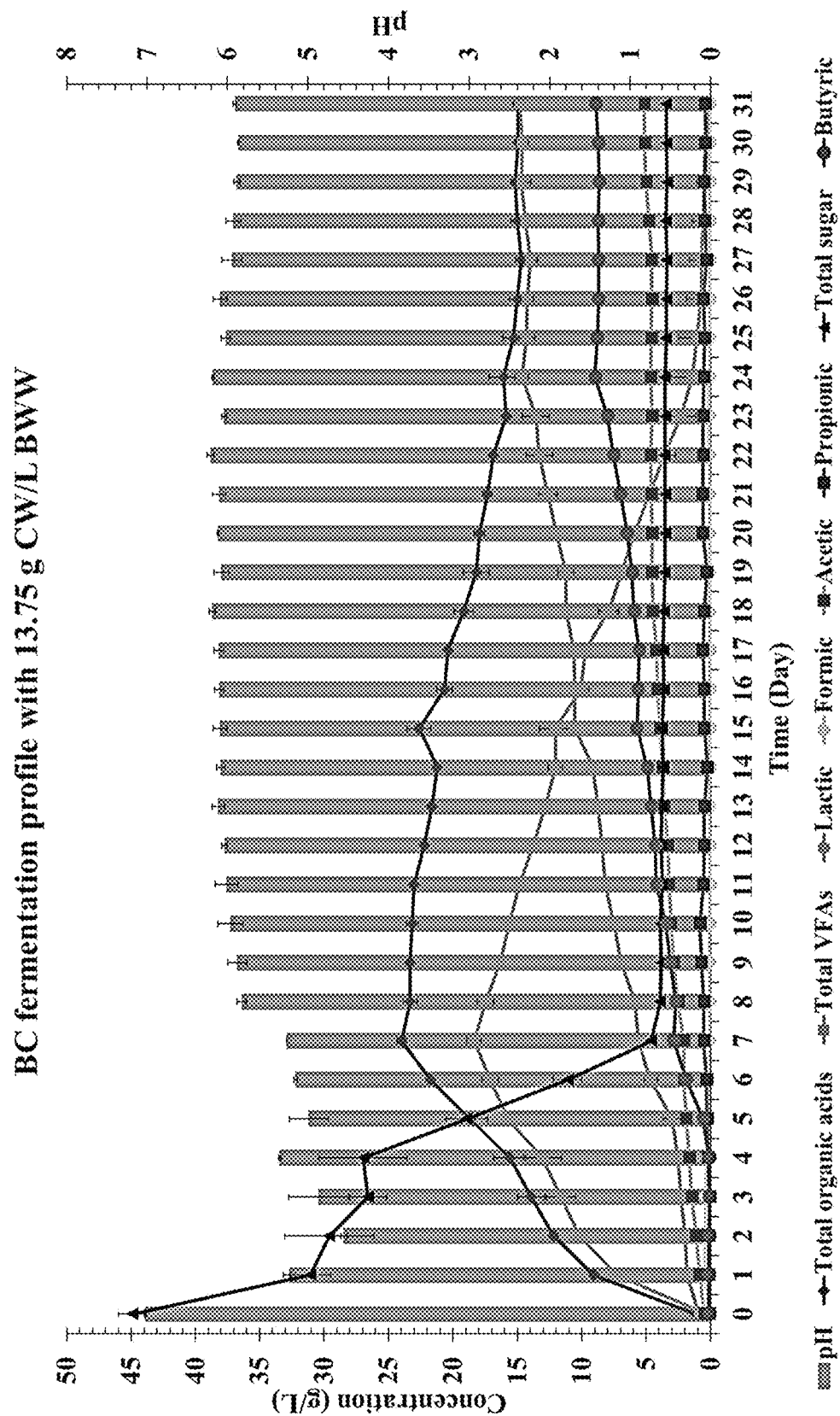
FIG. 5 is a graph of the fermentation profile of a brewery wastewater organic waste stream with an inocula including 13.75 g/L cheese whey.
Figure 6:
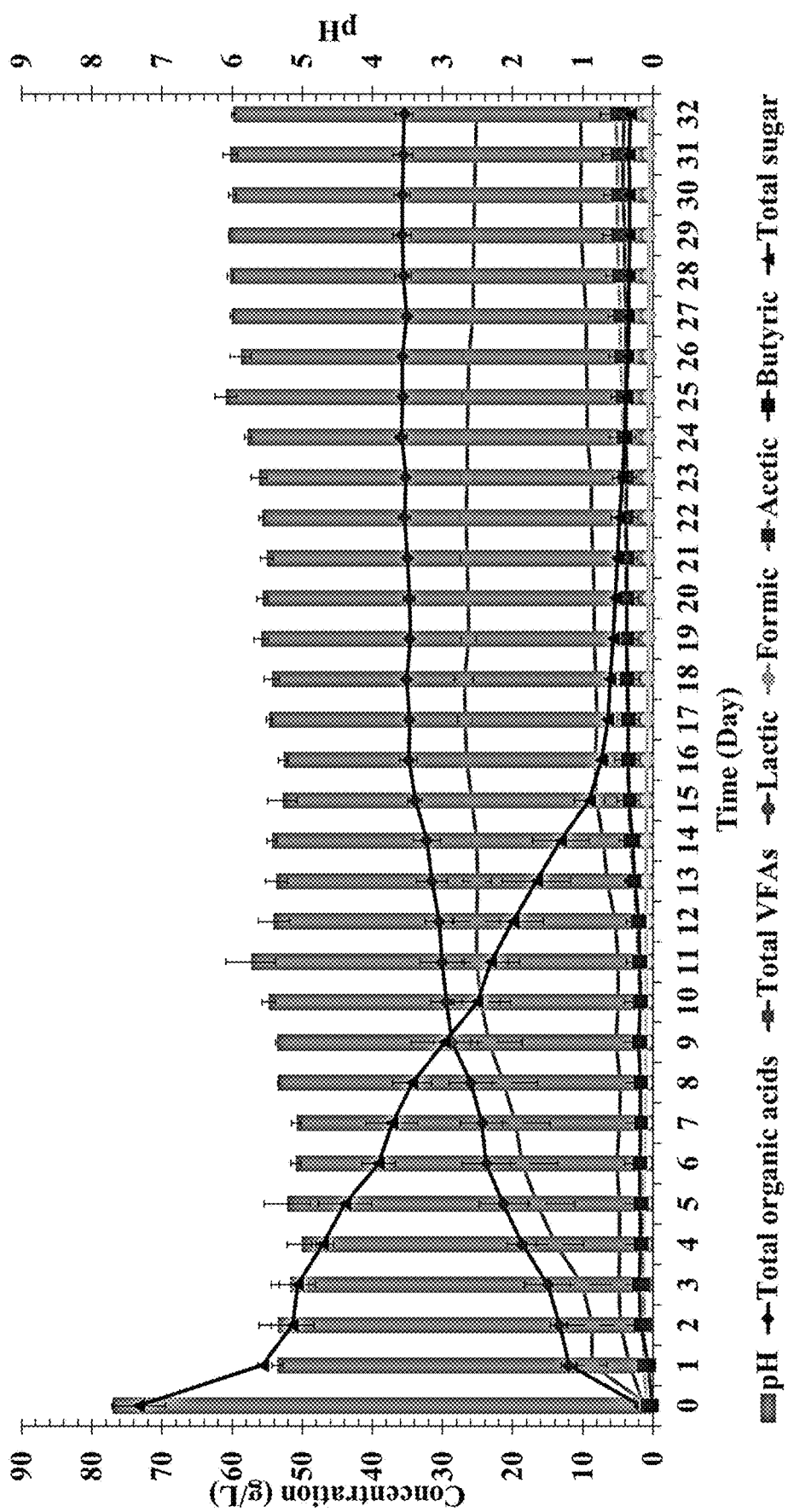
FIG. 6 is a graph of the fermentation profile of a brewery wastewater organic waste stream with an inocula including 38.12 g/L cheese whey.
Figure 7:
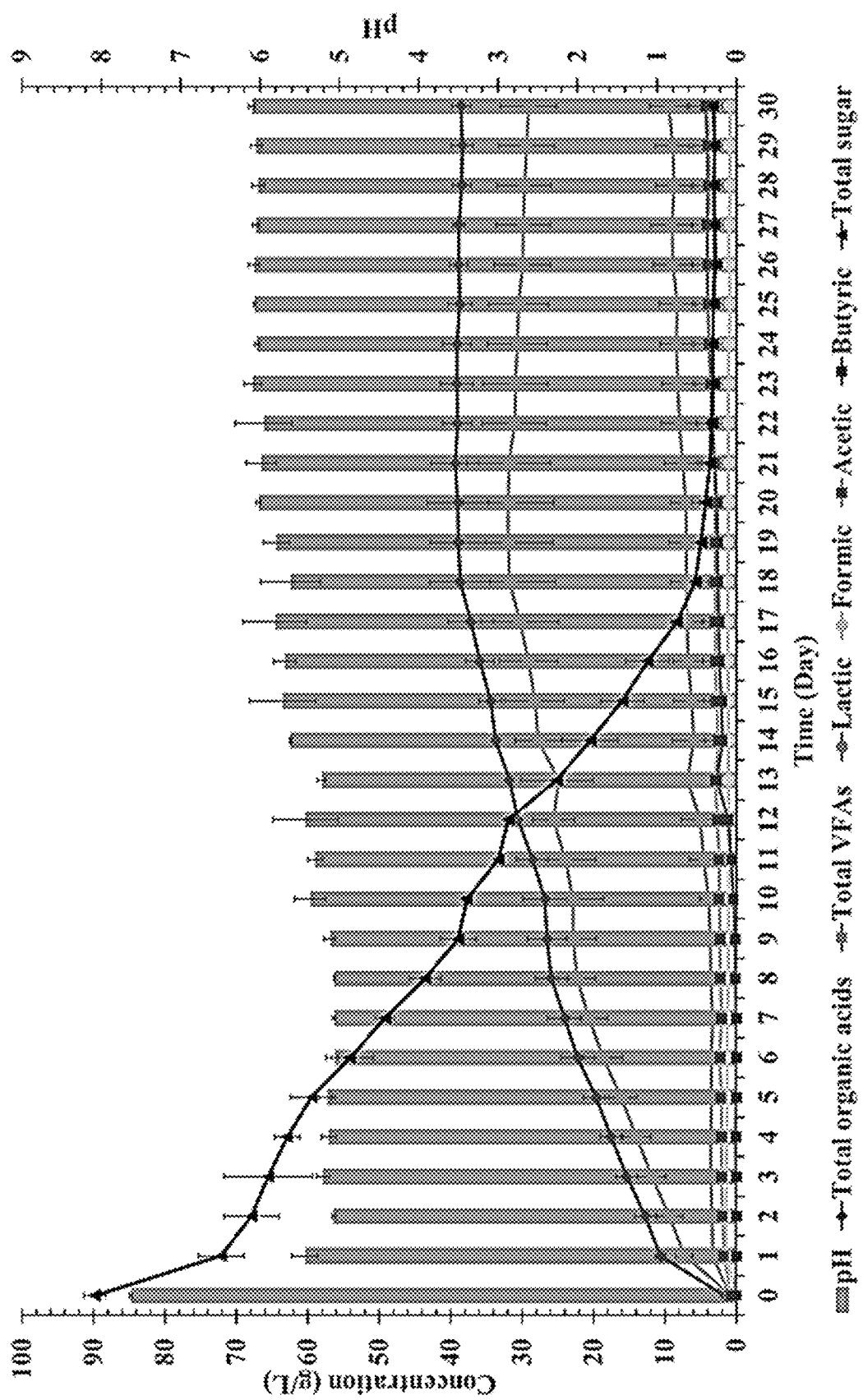
FIG. 7 is a graph of the fermentation profile of a brewery wastewater organic waste stream with an inocula including 50.00 g/L cheese whey.

The results for each of BC-I, BC-II, and BC-III are shown in FIGS. 5, 6, and 7, respectively. As can be seen from these results, at each of 38.12 g/L and 50 g/L concentrations of cheese whey in BWW (i.e., BC-II and BC-III), the concentration of total organic acids and lactic acid after 30 days was about 35-40 g/L and about 25-30 g/L, respectively. Each of the organic acid and lactic acid concentrations in these samples steadily increased, until plateauing at about 16-18 days of fermentation. These steady increases in organic acid and lactic acid corresponded to the steady decrease in the amount of total sugars, indicating conversion of the sugars into organic acids and ethanol. The amounts of VFAs, such as acetic acid and butyric acid, remained relatively constant throughout the fermentation, with a total VFA concentration of about 1 g/L or less.

In contrast, the sample with only 13.75 g/L cheese whey (i.e., BC-I) showed a rapid decline in total sugars, which reached its lowest concentration of about 5 g/L after only about 7 days of fermentation. The concentrations of organic acid and lactic acid similarly increased and reached peak concentrations around day 7, at about 25 g/L and 18 g/L, respectively. After reaching these peak concentrations, the results suggest that the lactic acid was further converted to butyric acid and acetic acid, which steadily increased in concentration after day 7. By day 30, the total VFA concentration in the sample was about 14 g/L, of which approximately 5 g/L was acetic acid and 9 g/L was butyric acid.

Example 2 demonstrates that higher concentrations of cheese whey in the brewery wastewater resulted in an increase in the organic acid production, but did not result in conversion of the lactic acid to VFAs, such as acetic acid and butyric acid. In contrast, when less cheese whey was present, lactic acid concentrations peaked after about 7 days, at which time the lactic acid was converted further to produce VFAs.

Example 3—Serum Bottle Batch Fermentation

Serum Bottle Batch Fermentation experiments were run in 0.5 L serum bottles, with a 0.4 L working volume with a variation of temperature. A 50 g/L cheese whey powder (CW) solution with brewery wastewater (BWW) was used as the feed. The solutions were buffered using NaOH/HCl to a target pH of 6. The inoculum tested was fermentation broth from 2-stage CSTR fermentation system originally from New Orleans Beach sediment. Each sample was tested in triplicate at a fermentation temperature of 40° C. or 55° C.

Figure 8A:
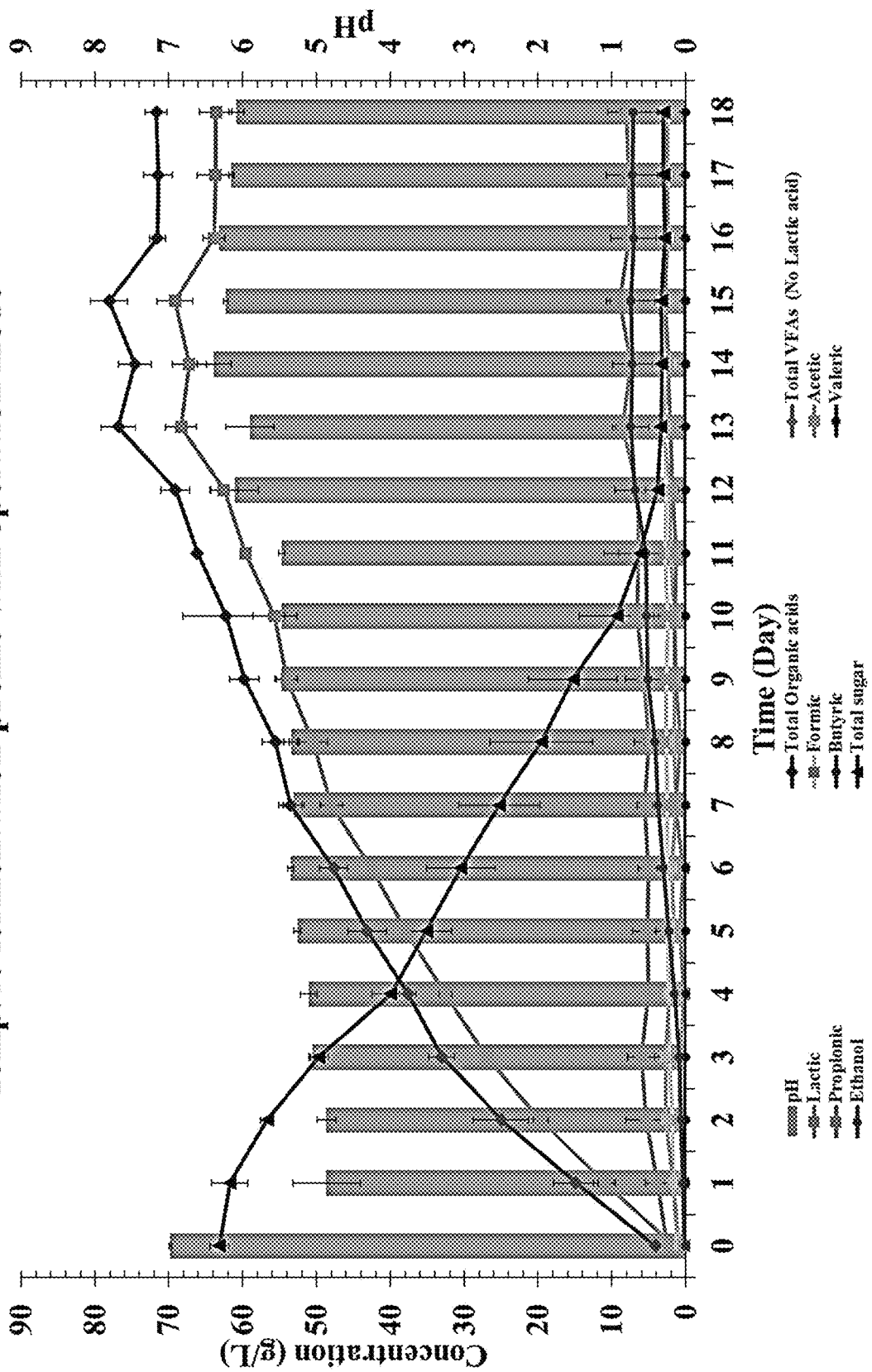
FIG. 8A is a graph of the fermentation profile of a brewery wastewater organic waste stream with an inocula including cheese whey at 40° C.
Figure 8B:
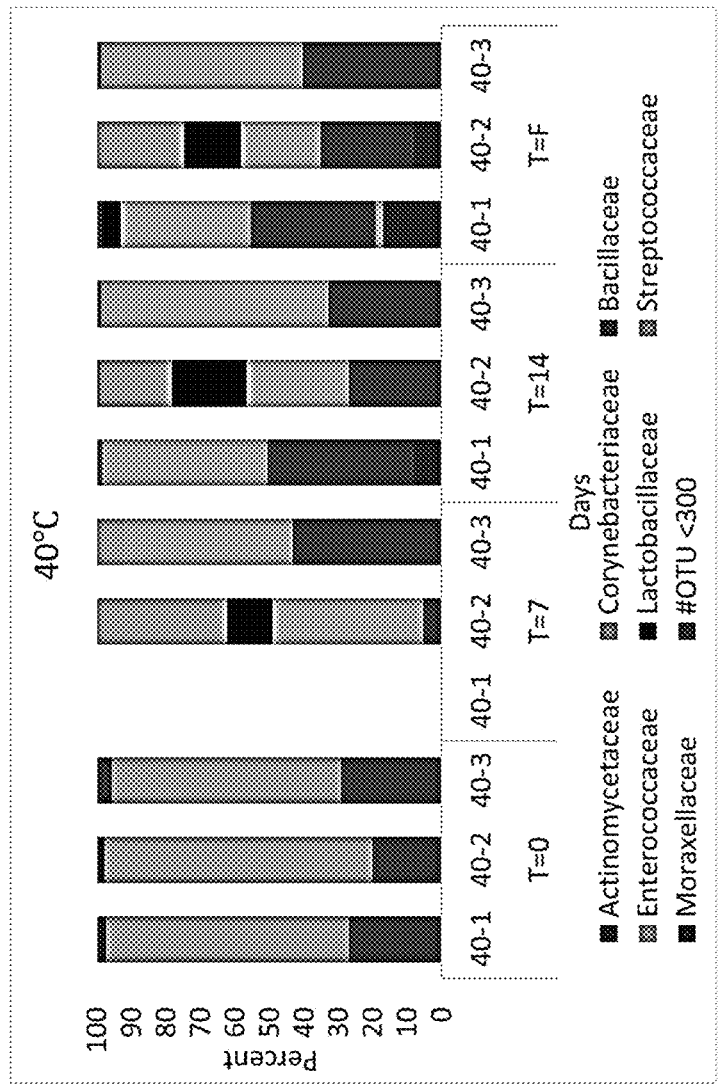
FIG. 8B is a 16S RNA analysis of the microbial community present in the fermentation of a brewery wastewater organic waste stream with an inocula including cheese whey at 40° C.
Figure 9A:
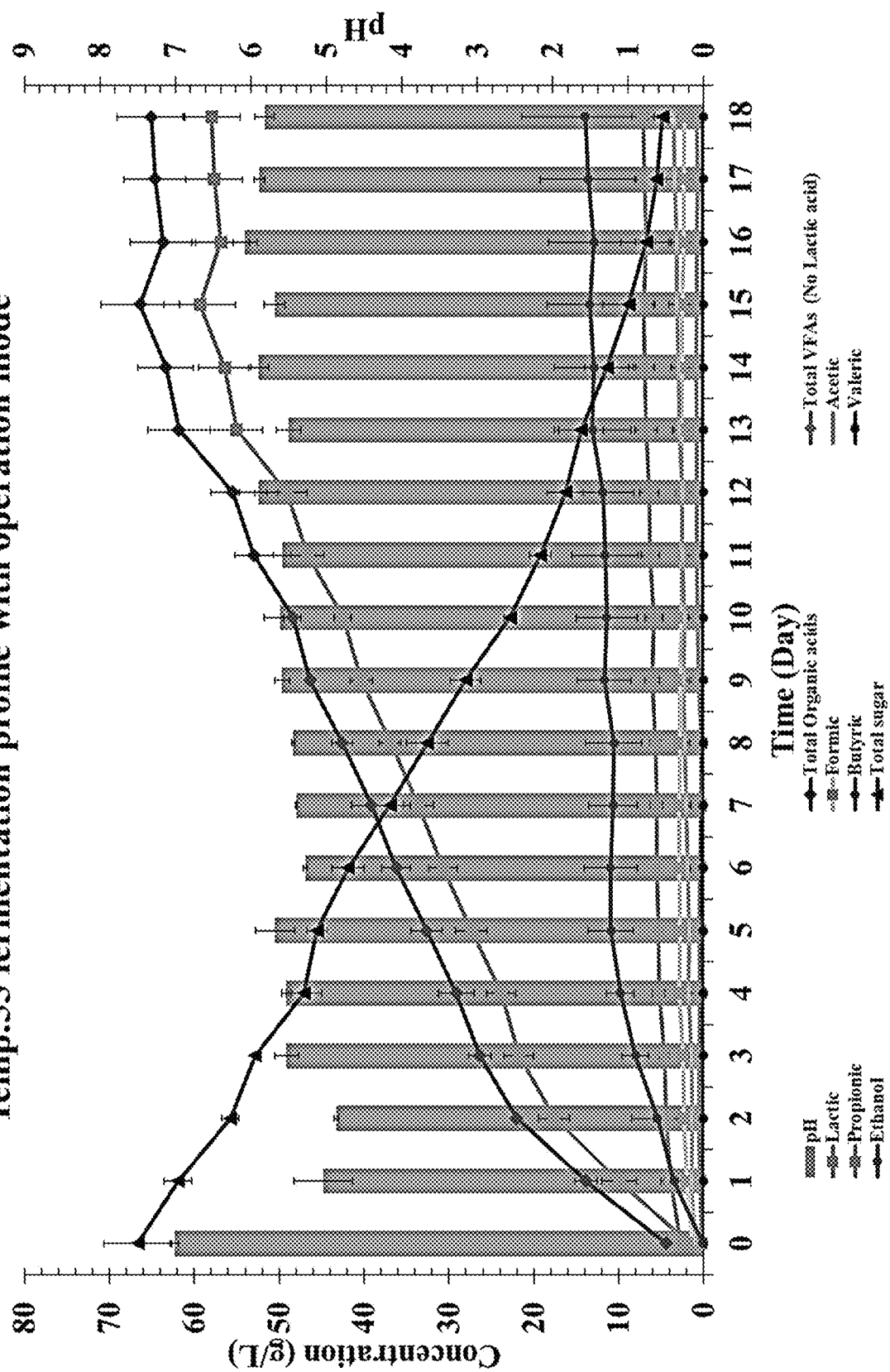
FIG. 9A is a graph of the fermentation profile of a brewery wastewater organic waste stream with an inocula including cheese whey at 55° C.
Figure 9B:
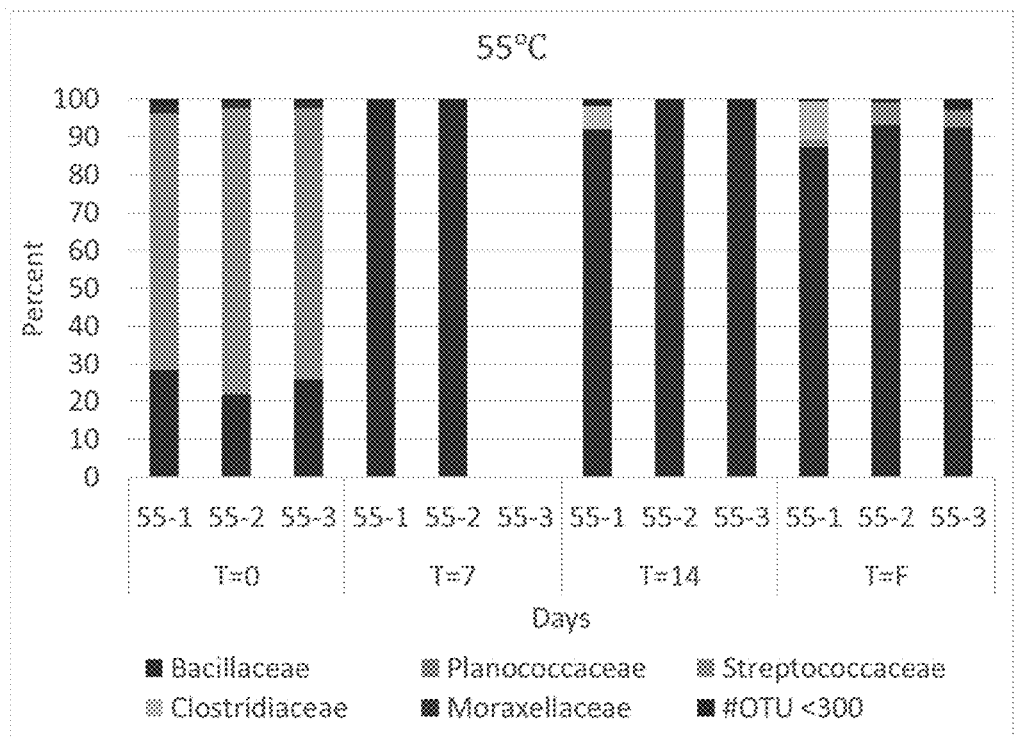
FIG. 9B is a 16S RNA analysis of the microbial community present in the fermentation of a brewery wastewater organic waste stream with an inocula including cheese whey at 55° C.

FIG. 8A shows the fermentation profile for the fermentation at 40° C. and FIG. 8B shows the associated microbial community which was generated by 16s RNA analysis as described above. FIG. 9A shows the fermentation profile for the fermentation at 55° C. and FIG. 9B shows the associated microbial community which was generated by 16s RNA analysis as described above. As seen in these figures, fermentation at 40° C. resulted in a higher diversity in microbial structure than fermentation at 55° C.

Figure 10A:
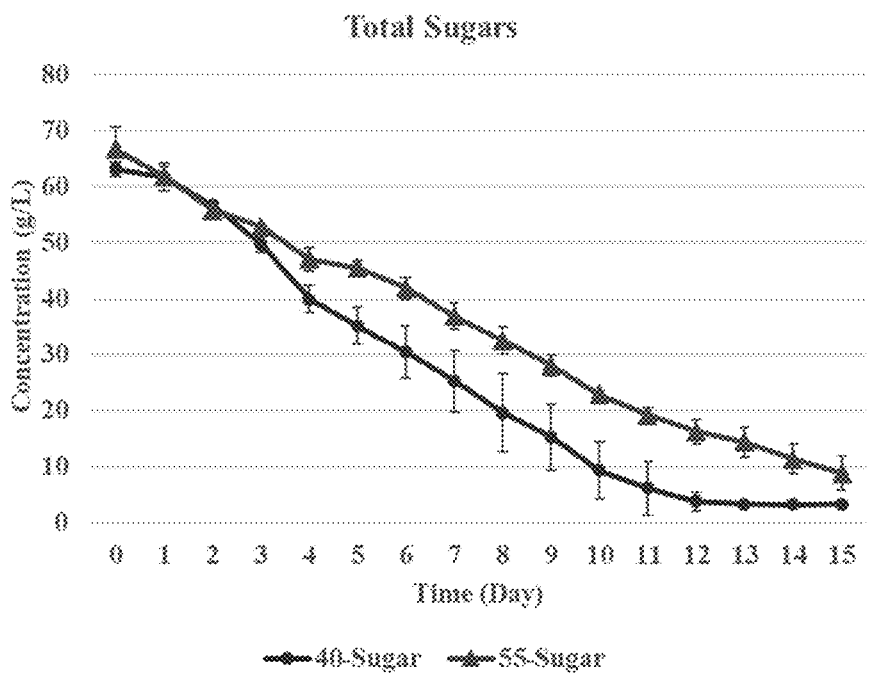
FIG. 10A is a graph of the temporal changes in the total sugar concentration during the fermentation of a brewery wastewater organic waste stream with an inocula including cheese whey at 40° C. and 55° C.
Figure 10B:
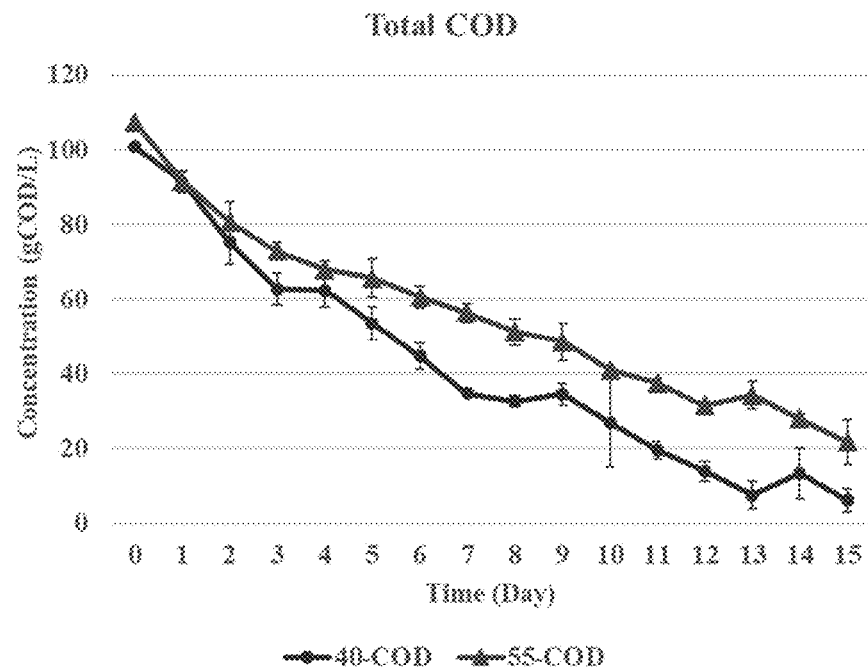
FIG. 10B is a graph of the temporal changes in total chemical oxygen demand (COD) concentrations during the fermentation of a brewery wastewater organic waste stream with an inocula including cheese whey at 40° C. and 55° C.
Figure 10C:
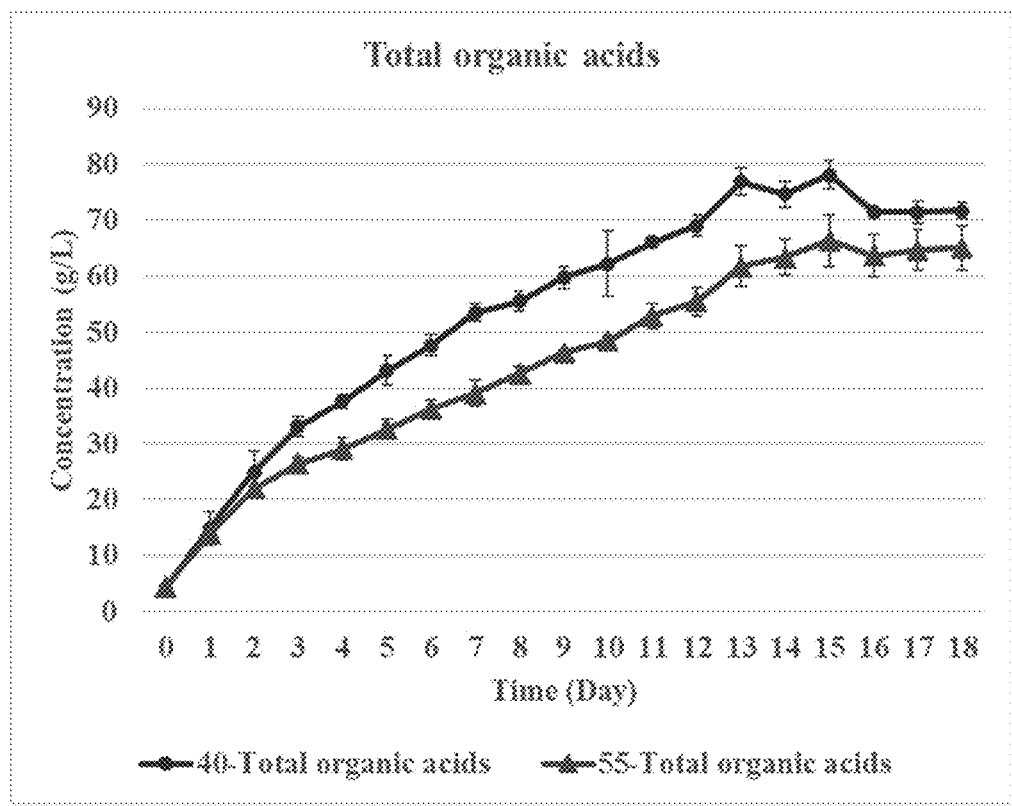
FIG. 10C is a graph of the temporal changes in total organic acid concentrations during the fermentation of a brewery wastewater organic waste stream with an inocula including cheese whey at 40° C. and 55° C.
Figure 10D:
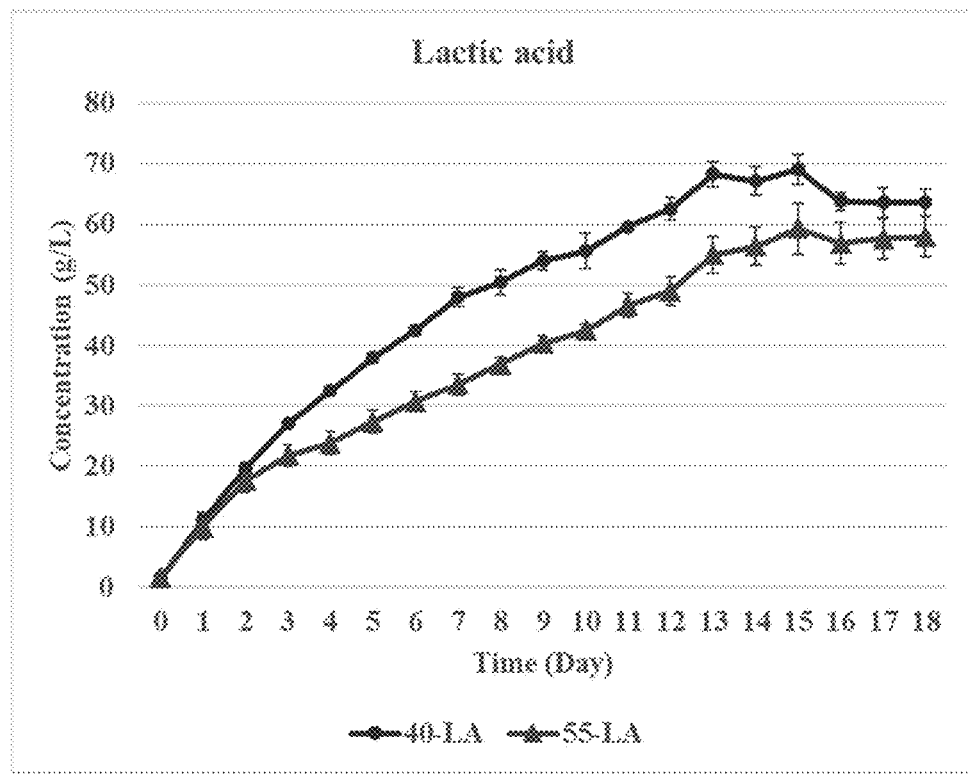
FIG. 10D is a graph of the temporal changes in total lactic acid concentrations during the fermentation of a brewery wastewater organic waste stream with an inocula including cheese whey at 40° C. and 55° C.
Figure 10E:
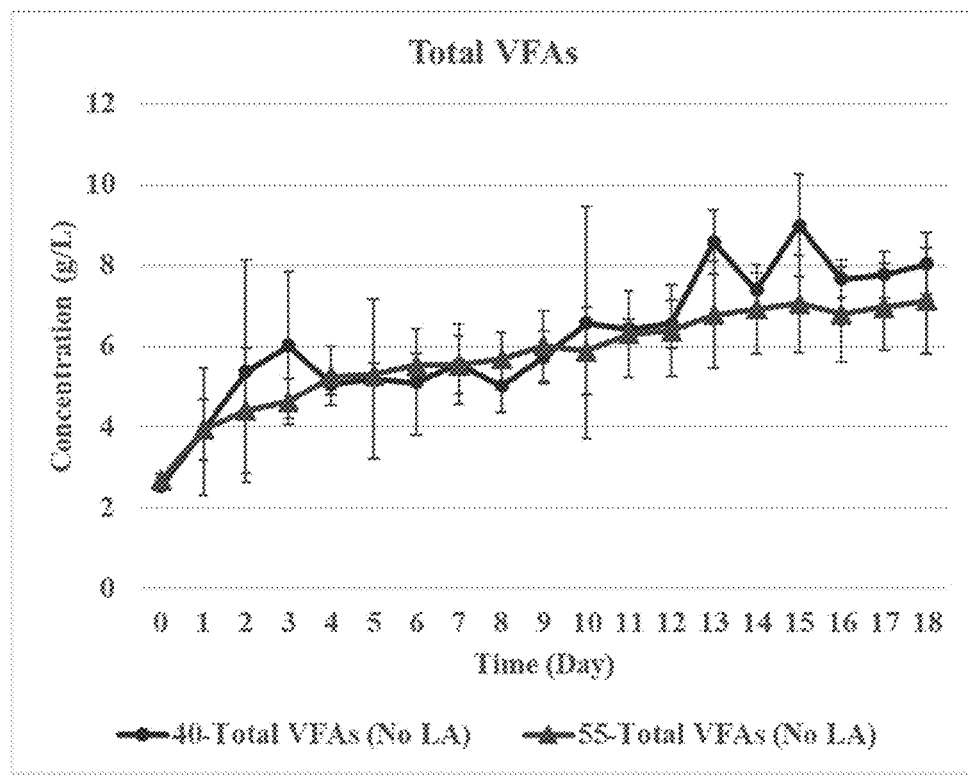
FIG. 10E is a graph of the temporal changes in total volatile fatty acid concentrations during the fermentation of a brewery wastewater organic waste stream with an inocula including cheese whey at 40° C. and 55° C.

As shown in FIGS. 10A and 10B, fermentation at 40° C. resulted in a faster reduction and overall reduced sugar concentrations and total COD concentrations. As shown in FIGS. 10C and 10D, the samples run at 40° C. also produced increased total organic acids, with increased lactic acid. There was no significant difference in total VFAs between fermentation at 40° C. and 55° C. (FIG. 10E).

Figure 11:
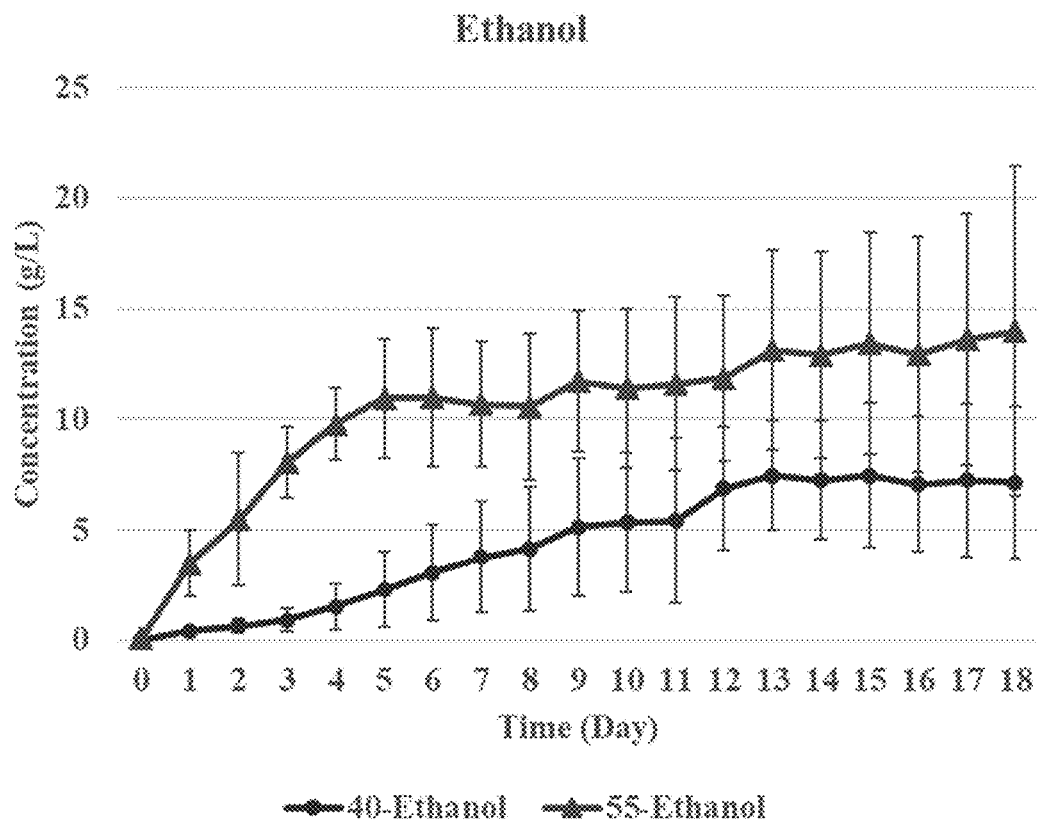
FIG. 11 is a graph of the temporal changes in ethanol concentrations during the fermentation of a brewery wastewater organic waste stream with an inocula including cheese whey at 40° C. and 55° C.
Figure 12A:
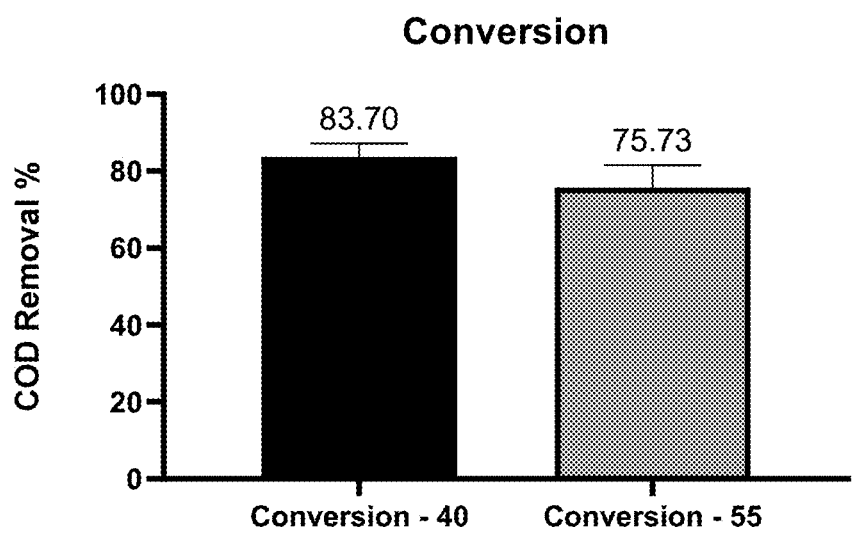
FIG. 12A is a graph of the conversion of COD during the fermentation of a brewery wastewater organic waste stream with an inocula including cheese whey at 40° C. and 55° C.
Figure 12B:
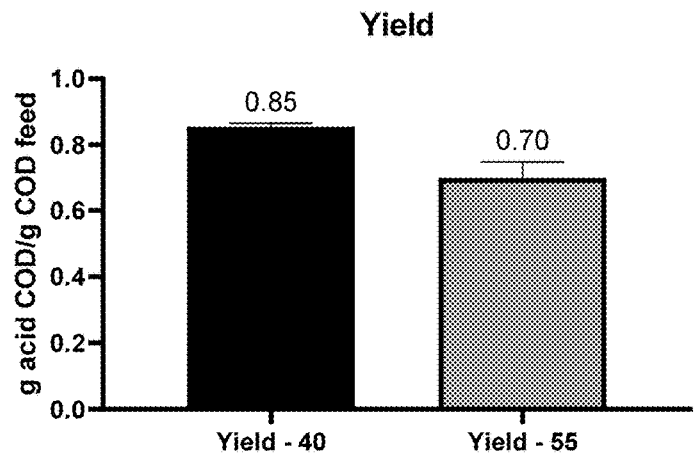
FIG. 12B is a graph of the yield of the acid COD to feed COD ratio during the fermentation of a brewery wastewater organic waste stream with an inocula including cheese whey at 40° C. and 55° C.

By contrast, for ethanol production, fermentation at 55° C. was found to be higher than that of 40° C., as shown in FIG. 11. This example demonstrates that solventogenesis occurred due to high temperature and organic acids in the digester environment. FIGS. 12A and 12B show that a reduced amount of COD was removed by fermenting at 55° C. as compared to 40° C., and the ratio of acid COD to feed COD was also less.

Example 4—Batch Fermentation in 14 L Fermenters

Batch fermentation experiments were run in 14 L bioreactors, with a 9 L working volume to test the variation of CW concentration. The fermentation temperature was 40° C. and the fermentation was run in 9 L batches. The feed was CW in BWW solution or CW in deionized (DI) water solution at varying concentrations as outline in the table below. The samples were buffered to a target pH of 6 with NaOH/HCl. The inoculum was a mixture fermentation broth from previous batch fermentation described in Example 3 originally from New Orleans beach saline and treated with inoculum of kefir, probiotics, and cheese from Example 1. The 14 L fermenter experiments were conducted with the same feedstock composition and fermenter operations. Bio 9-1 was run first, then Bio 9-2 and 9-3 were run. During the experiments, the pH probe was failed at Bio 9-2 and shifted the fermenters towards the production of VFAs, more specifically butyric acid.

| | Group | |
|---|---|---|
| | Bio 9-1 | Bio 9-2 & 9-3 |
| Feedstock | 77g/L CW in BWW | 77 g/L CW in BWW |

Figure 13A:
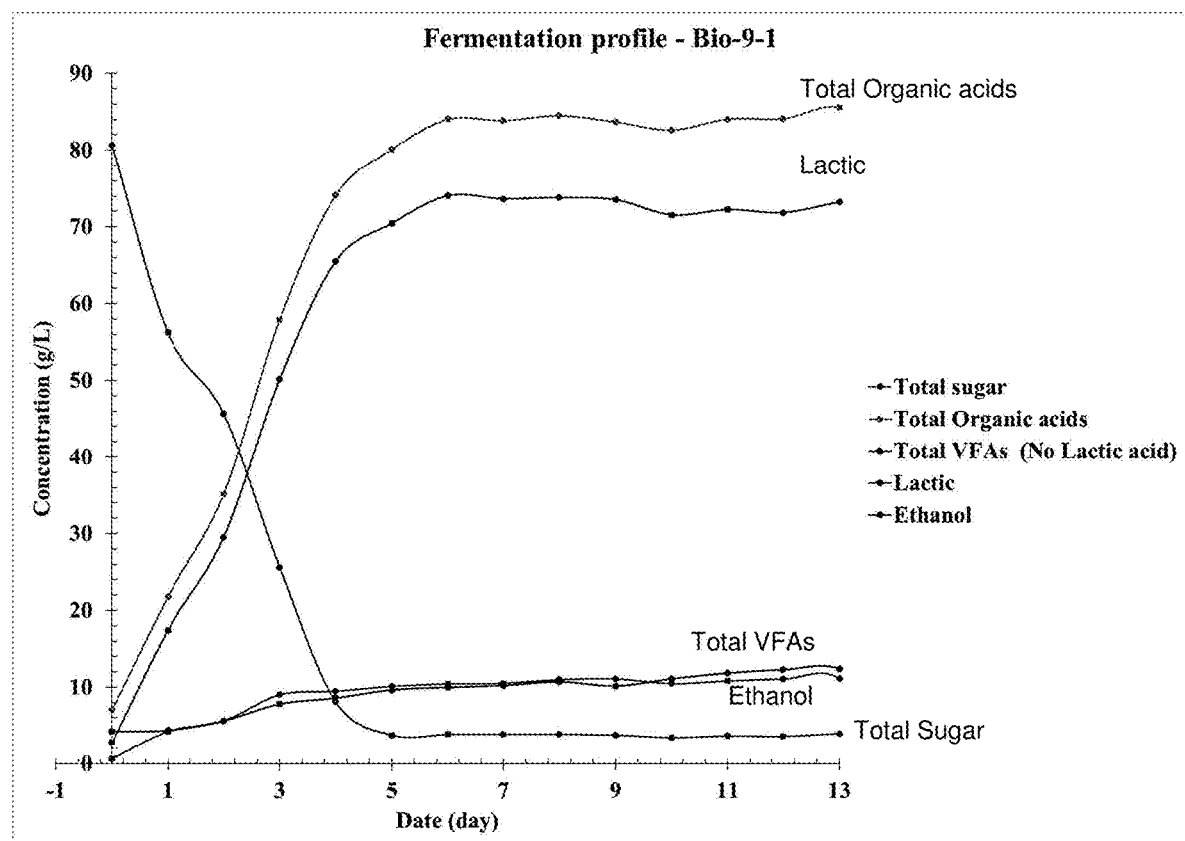
FIG. 13A is a graph of the fermentation profile of a brewery wastewater organic waste stream with an inocula including 77 g/L cheese whey.
Figure 13B:
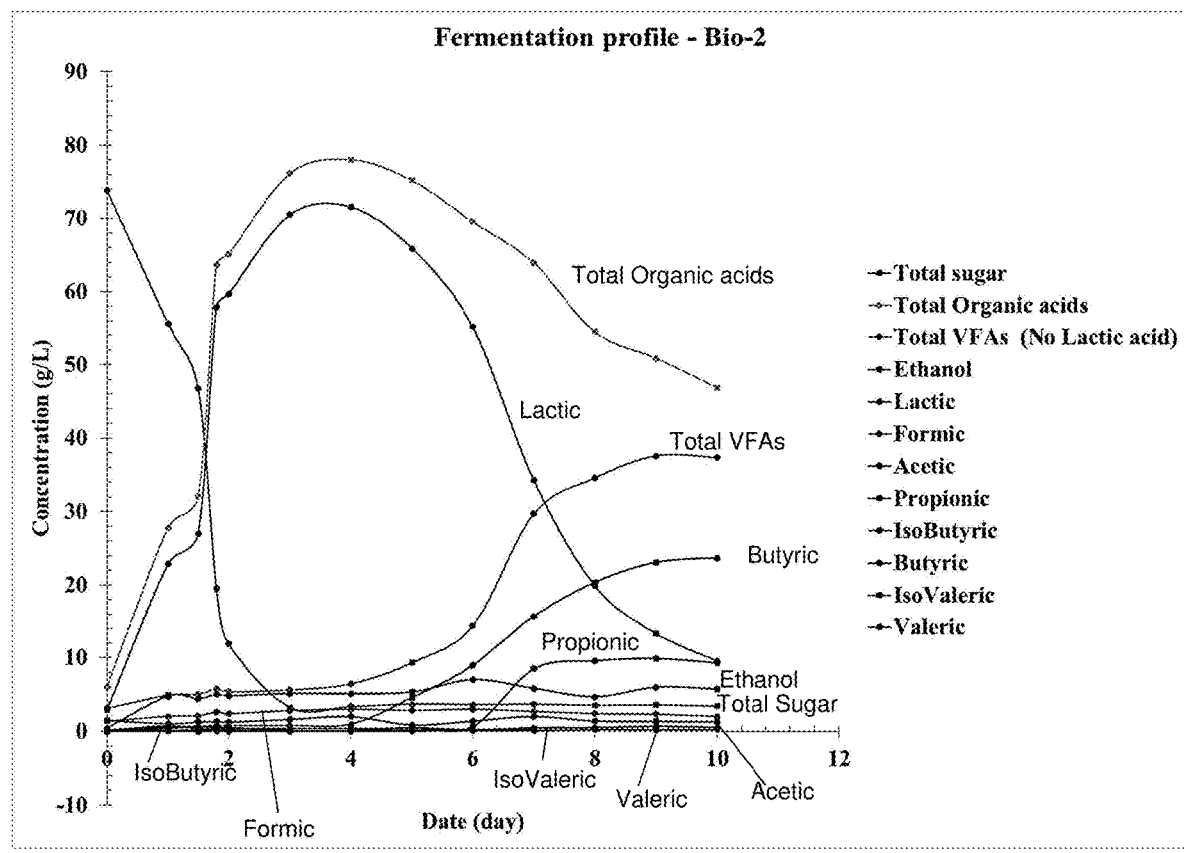
FIG. 13B is a graph of the fermentation profile of a brewery wastewater organic waste stream with an inocula including 77 g/L cheese whey.
Figure 13C:
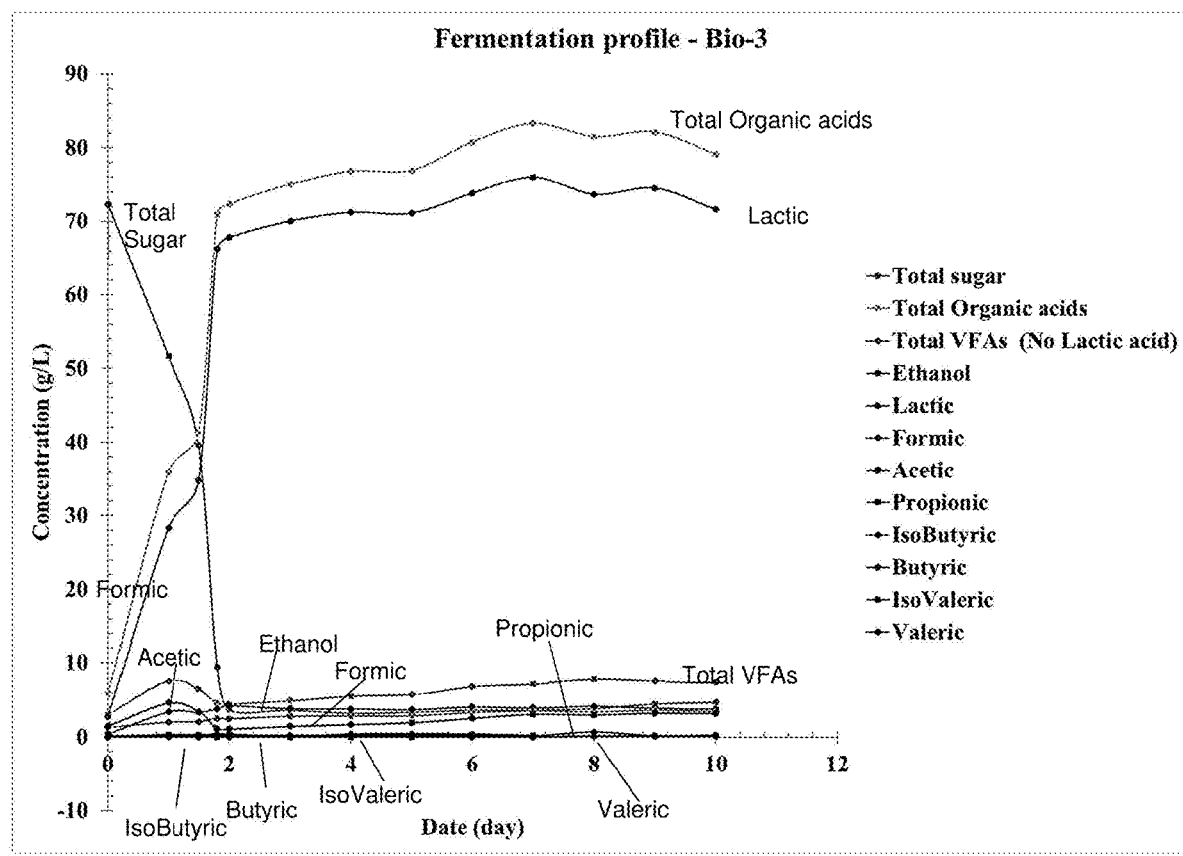
FIG. 13C is a graph of the fermentation profile of a brewery wastewater organic waste stream with an inocula including 77 g/L cheese whey.
Figure 14:
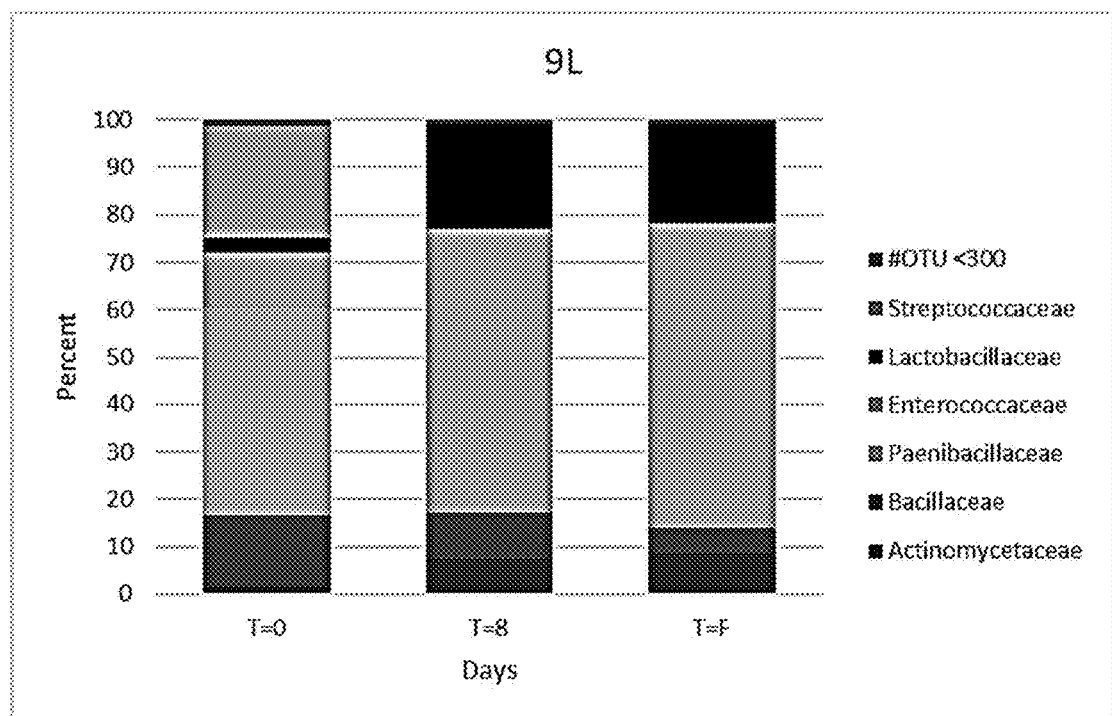
FIG. 14 is a temporal 16S RNA analysis of the microbial community present in the fermentation of the brewery wastewater organic waste stream with an inocula including 77 g/L cheese whey as shown in FIG. 13A.

The results for Bio 9-1, Bio 9-2, and Bio 9-3 are shown in FIGS. 13A, 13B, and 13C, respectively. As shown in FIG. 13A, Bio 9-1 resulted in about 73 g/L lactic acid and about 10 g/L VFAs, with an overall acid concentration of about 85 g/L. The microbial compositional structure of Bio 9-1 at different time points of the fermentation can be seen in FIG. 14.

As shown in FIG. 13C, Bio 9-3 resulted in about 76 g/L lactic acid and about 7 g/L VFAs, with an overall acid concentration of about 83 g/L. These results were similar to those of Bio 9-1 and suggest that the isolated and enriched mixed culture is highly robust, resilient, and productive.

In contrast with Bio 9-1 and Bio 9-3, Bio 2 peaked in lactic acid concentration at about day 4 (FIG. 13B). The maximum lactic acid concentration of Bio 2 was 71 g/L, and the maximum concentration of VFAs, which peaked at around day 10 of the study, was about 37.5 g/L. These data suggested that the pH of the digester environment was important and provided flexibility in running the fermenters like a biorefinery. This allows for the production of targeted products. The experimental results showed that low pH (<6.0) directs the fermentation towards the lactic acid production while the pH value (>6.0) results in the conversion of lactic acid to volatile fatty acids.

Example 5—Separation of Acetic Acid

Each of ion-exchange (IX) resins, nanofiltration (NF) membranes and reverse osmosis (RO) membranes for the separation and purification of acetic acid were compared.

Acetic acid was selected as a representative low-molecular weight organic acid produced using the methods of the disclosure. Specifically, commercially available IX resins and membrane materials were used to separate acetic acid from aqueous solution under conditions that emulate real anaerobic organic waste, which typically contains about 4-56 g/L acetic acid depending on the inoculum and waste feedstocks. In summary, the adsorption equilibrium, adsorption kinetics, and desorption/recovery for commercially available IX resins with varying polymer matrix structures and basic functionalities were characterized. In addition, acetic acid separation performance (permeability and selectivity) by several commercially available NF/RO membranes over a range of applied pressures, concentrations, and pH values were characterized. The results provide insight into factors that affect acetic acid separation and purification and provide a side-by-side comparison of two alternative separation techniques.

Materials. Five IX resins with a range of physicochemical properties (Table 1) were employed. IRN-78 and A26 are strong-base anion-exchange resins with gel and macroporous structures, respectively. IRN-67 and WA10 are gel-type weak-base anion exchange resins whereas DOWEX-66 is a macroporous weak-base anion-exchange resin. Each resin was used as received from the manufacturer and was not subjected to further treatment.

TABLE 1

Physicochemical Properties of IX Resins

| | Resin | | | | |
|---|---|---|---|---|---|
| | IRN-78 | A26 | IRA-67 | DIAION WA10 | DOWEX-66 |
| Type | Strong-base | Strong-base | Weak-base | Weak-base | Weak-base |
| Matrix | Styrene-DVB | Styrene-DVB | Acrylic | Acrylic-DVB | Styrene-DVB |
| Functional group | Trimethyl-ammonium | Quaternary ammonium | Tertiary amine | Tertiary amine | Tertiary amine |
| Ionic form | OH⁻ | OH⁻ | Free base | Free base | Free base |
| Exchange capacity (eq/L) | ≥1.20 | ≥0.80 | ≥1.60 | ≥1.20 | ≥1.60 |
| Moisture content (%) | 54-60 | 66-75 | 56-64 | 63-69 | 40-46 |
| Particle size (μm) | 580-680 | 560-700 | 500-750 | 300-1180 | 300-1200 |
| pKa | N/A (strong base) | N/A (strong base) | 9.0 | 8.8 | 6.4-8.5 |

In addition, five thin-film composite (TFC) membranes with variable polyamide chemistries (Table 2) were employed. The DuPont NF (denoted as NF*) and DuPont NF270 membranes have a semi-aromatic polyamide active layer, whereas the DuPont NF90, DuPont BW30XFR, and GE-SE membranes have a fully aromatic active layer.

TABLE 2

Physicochemical properties of membranes

| Name | Type | Pore size/MWCO (Da) | Polymer | pH range | Salt rejection | Water permeability ($L \cdot m^{-2} \cdot h^{-1} \cdot bar^{-1}$) |
|---|---|---|---|---|---|---|
| NF270 | NF | ~200-400 | Polyamide-TFC | 2-11 | >97.0% MgSO₄ | 11.03 |
| NF90 | NF | ~200-400 | Polyamide-TFC | 2-11 | >98.7% MgSO₄ | 8.92 |
| NF* | NF | ~200-400 | Polyamide-TFC | 2-11 | >98.0% MgSO₄ | 6.53 |
| BW30XFR | RO | ~100 | Polyamide-TFC | 2-12 | >99.5% NaCl | 2.91 |
| SE | RO | ~100 | Polyamide-TFC | 1-11 | >99.0% NaCl | 1.32 |

Adsorption with IX Resins

Batch Adsorption Experiments. Equilibrium experiments were performed in a thermostatic shaker for 24 h at 25° C. and 150 rpm. For each resin, the effect of resin dosage (0.6-30 g wet resin) was investigated in 50 mL of 9 g/L acetic acid solution (pH=6.3). The effect of initial solute concentration (5-25 g/L acetic acid, pH=6.3) was investigated using a resin dosage of 2 g wet resin in 50 mL solution. Finally, to evaluate the effect of initial pH (2.7-7.2) on adsorption performance, experiments employed 2 g of select IX resins (IRN-78 and IRA-67) mixed with 9 g/L acetic acid. In all adsorption experiments, the solution pH was adjusted to the desired value by dropwise addition of sodium hydroxide (NaOH) prior to adding resin. All equilibrium experiments were conducted in triplicate. Initial and equilibrium concentrations were measured via high performance liquid chromatography (HPLC).

Kinetic experiments were performed in 250 mL flasks that were continuously stirred at 600 rpm to enhance bulk diffusion. Separate mixtures of IRA-67 and IRN-78 were prepared by adding 2 g of resin to 200 mL of 9 g/L acetic acid solution (pH=6.3) at 25° C. Duplicate experiments were run for 180 min each with effluent samples (1.5 mL/sample) collected throughout the duration of the experiment. Again, initial and effluent samples were measured via HPLC and used in the kinetic models.

Column Separation. Breakthrough curves and resin reusability experiments were performed in a glass column (1.0 cm I.D. and 30.5 cm height; ChromaFlex, Kimble, Rockwood, TN). IRN-78 resin (5 g, particle density 1.2 g/mL, Bed volume (BV) 4.167 mL) was wet-settled in the center of the column with glass beads and glass wool packed symmetrically in both the inlet and outlet. Acetic acid solution (9 g/L, pH 6.3) was delivered from the top of the column at 1.00 mL/min (14.4 BV/hr) flow rate using a peristaltic pump (Masterflex L/S Digital Pump; Cole Parmer, Vernon Hills, IL) at 25° C. Samples were collected from the effluent every 3.5 min for over 2 h and measured using HPLC. The pH values of these samples were also measured simultaneously as a tool to monitor the column adsorption progress. After each adsorption cycle, the column was washed with excess NaOH (200 mL, 1 N) by recirculation for 6 h to desorb all acetate and regenerate the resin, confirmed via HPLC analysis of the NaOH effluent solution. Finally, the resin column was washed with Milli-Q water (18 MΩ×cm⁻¹ resistivity) until the pH of effluent was equivalent to the initial column pH (about 9.3). The adsorption-regeneration cycle was repeated a total of 10 times. To ensure that acetic acid solution was completely flushed out during the regeneration step, the mass balance of acetate was calculated according to Equation 1, below:

$$\text{Mass balance} = \frac{\text{mass of acetate recovered during regeneration}(g)}{\text{mass of acetate extracted during adsorption}(g)} \quad (1)$$

Results from IX Resin Studies

Equilibrium studies. The effect of the amount of IX resin on adsorption of acetic acid was investigated by varying the resin dosage while maintaining constant acetic acid concentration. For all resins, the removal of acetic acid from solution increased as resin dosage increased. Compared to the weak-base resins, both strong-base anion-exchange resins showed the highest acetic acid removal. At each selected wet resin dosage, IRN-78 achieved the highest acetic acid removal ranging from 13.0% at 0.6 g wet resin to 95.1% at 30 g wet resin. The next-best performing resin was A26 (10.0% removal at 0.6 g wet resin, 93.1% at 30 g), followed by DOWEX-66 and WA10, respectively. In terms of acetic acid removal, the least effective resin was IRA-67, which only removed 1.9% acetic acid at 0.6 g wet resin and 15.3% at 30 g wet resin.

Variation of the initial acetic acid concentration was also investigated using different acetic acid concentrations with a constant resin dosage. For all resins tested, with increased initial acetic acid concentration (from 5 to 25 g/L, initial pH=6.3), the percentage of acetic acid removal decreased. Without intending to be bound by theory, this decrease in removal efficiency was attributed to the saturation of accessible IX sites at higher acetic acid concentrations. The most significant decrease (about 70%) was observed with IRN-78 resin whereas the least impact was observed with the IRA-67 resin (about 15% decrease). Despite these pronounced changes in removal, IRN-78 demonstrated the highest percentage removal of acetic acid at all concentrations (55.9% at 5 g/L and 16.7% at 25 g/L whereas IRA-67 had the lowest percent removal of acetic acid (approximately 3%) over the range of concentrations investigated.

The effect of initial acetic acid concentration on equilibrium adsorption capacity (qe) was also observed. For all resins, qe increased as initial acetic acid concentration increased from 5 to 25 g/L. For strong-base anion exchange resins IRN-78 and A26, qe increased by 47.3% and 58.6%, respectively. In contrast, for weak-base anion exchange resins IRA-67, WA10, and DOWEX-66, qe increased by 322%, 277% and 186%, respectively. The maximum qe was 104 mg acetic acid/g wet resin at acetic acid concentration of 25 g/L with IRN-78.

Adsorption isotherms. Two adsorption isotherms—Langmuir and Freundlich—were used to evaluate the equilibrium behavior. The Langmuir isotherm assumes a monolayer adsorption of molecules onto a surface of finite, localized, identical, and equivalent adsorption sites, which are equally accessible for interaction. A linear plot of the equilibrium concentration $C_e$ divided by $q_e$ versus $C_e$ indicated that the Langmuir isotherm was suitable for the adsorption of acetic acid (pH>pK$_a$) onto strong-base anion-exchange resins (IRN-78 and A26, $R^2$>0.99). However, some deviations were observed for weak-base anion exchange resins (DOWEX-66, WA10, and IRA-67). IRN-78 achieved the highest maximum monolayer adsorption capacity ($q_m$=110.86 mg acetic acid/g wet resin), followed by A26 ($q_m$=93.11 mg acetic acid/g wet resin). Based on the Langmuir constant (KL), IRN-78 had the highest adsorption energy among the tested resins. To better interpret KL, a dimensionless constant known as separation factor (RL) was used. This factor was in the range of 0 to 1 for IRN-78, A26, and Dowex-66, which indicated a favorable adsorption process between these resins and acetic acid at pH greater than pK$_a$.

The Freundlich isotherm describes a multilayer adsorption with interaction between adsorbed molecules onto heterogeneous surfaces, assuming adsorbent surface sites have a spectrum of different binding energies. A linear form of the Freundlich isotherm, prepared by plotting $\log_{10}$ qe versus $\log_{10}$ Ce, indicated that the Freundlich isotherm fit all resins tested (R2>0.96). Meanwhile, the slope (0<1/n<1) was the measure of adsorption surface heterogeneity, becoming more heterogeneous as it approached zero. Both IRN-78 and A26 had much smaller values of 1/n than weak-base anion-exchange resins, indicating greater surface heterogeneity and stronger adsorbent-adsorbate bonds formed for acetic acid adsorption with strange-base anion exchange resins.

pH Effects. To investigate the effects of initial solution pH on q$_e$ for each of these resins, a constant resin dosage of 2 g was used in conjunction with a total acetic acid plus acetate concentration of 9 g/L. When the initial pH of solution was below the pK$_a$ (4.76) of acetic acid, the weak-base anion-exchange resin (IRA-67) was the superior of the two resins. Specifically, at an initial pH of 2.67 and 3.63, IRA-67 had a constant q$_e$ of 148 mg acetic acid/g wet resin. However, q$_e$ for the IRA-67 significantly decreased when the initial solution pH surpassed the pK$_a$ of acetic acid. In contrast, the strong-base anion exchange resin (IRN-78) performed significantly better when the initial pH of the solution was higher than the pK$_a$ of acetic acid, with q$_e$ ranging from 82 to 114 mg acetic acid/g wet resin. Although q$_e$ for both resins decreased with the increasing equilibrium pH, the q$_e$ of IRA-67 sharply decreased once the pH exceeded pK$_a$, whereas q$_e$ of IRN-78 gradually decreased with increasing pH. In addition, since biochemical production of acetic acid usually has a fermentation pH around 6-7, the results suggest that IRN-78 was a good candidate for use as an IX adsorbent for acetic acid removal in biochemical processes.

Kinetics. Aside from adsorption equilibria, adsorption kinetics also play a role in the applicability of any adsorbent because they define the efficiency of the adsorption process. Adsorption kinetics were studied for IRN-78 and IRA-67 by applying pseudo-first-order and pseudo-second-order kinetic models to experimental data collected using constant resin dosage of 2 g and initial acetic acid concentration of 9 g/L at pH=6.3. The results demonstrated that both IRN-78 and IRA-67 reached equilibrium within 60 min. Compared with pseudo-first-order, the pseudo-second-order model was more suitable to describe the adsorption kinetics for acetic acid onto IRN-78 and IRA-67 (R2>0.99). This suggested that for both resins, adsorption was the rate-limiting step as opposed to diffusion of the acetic acid to the surface of the anion-exchange resin. The calculated adsorption rate constants for IRN-78 and IRA-67 were 0.20 and 0.04 g/(mg·min), respectively. The calculated adsorption capacities for IRN-78 and IRA-67 were 101 and 17.8 mg acetic acid/g wet resin, respectively; therefore, IRN-78 was the superior of the two resins.

Breakthrough curves. To understand the adsorption performance in a column operated in a continuous mode, as well as the effects of resin regeneration on adsorption performance, the resin adsorption column was packed with IRN-78 to obtain breakthrough curves using 9 g/L acetic acid solution at pH 6.3 as the influent. Once the column was sufficiently washed, 10 consecutive adsorption-regeneration cycles were conducted to generate average breakthrough curves at the influent rate of 14.4 BV/hr. The results indicated that the column was able to capture nearly 100% acetate from influent for the initial 2.5 BV. Between 2.5 and 10 BV, around 94% of acetate from the influent was adsorbed by the column. However, the concentration of acetate in the effluent increased sharply between 10 and 20 BV, indicating saturation of IRN-78 resin. After 20 BV, additional acetate removal from influent solution was negligible. Therefore, the breakthrough curve had implications for fixed bed column operation and regeneration.

The adsorption capacity of the column in each cycle was calculated based on the masses of acetate captured and wet resin loaded into the column. The average value (107.6±2.45 mg acetic acid/g wet resin) was close to the value obtained by Langmuir isotherm ($q_m$=110.9 mg acetic acid/g wet resin) in the equilibrium study with fresh resin IRN-78. After each adsorption process, the captured acetate in the column was washed out using NaOH solution and Milli-Q water. The mass balance of the acetate in each adsorption-regeneration cycle was calculated using Eq. (1), and the average was 96±4% for the 10 cycles. These mass balances suggested the adsorption capacity of the IRN-78 packed column was not severely affected by repetitive adsorption and regeneration.

Crossflow NF/RO Membrane Filtration Experiments

Water permeability and solute rejection of NF or RO membranes were tested using a crossflow filtration unit (CF042D, Sterlitech, WA). Prior to solute permeation experiments, each membrane was rinsed in Milli-Q water overnight. Then, each membrane was compacted at 27.6 bar using Milli-Q water until the permeate flux ($J_v$) was constant, after which the pure-water permeabilities of each membrane were measured. The maximum testing pressure was approximately 27.5 bar; thus, 27.6 bar was chosen as the compacting pressure to ensure the membrane would not compact further during the subsequent experiments.

Solute permeation experiments were performed with acetic acid solutions at a crossflow velocity of 0.42 m/s. Several acetic acid solutions with different concentrations (9-80 g/L) and pH (2.7-9.7) were prepared and used to assess the feasibility of the NF/RO separation for acetic acid solution. The solution pH was adjusted by dropwise addition of NaOH. In all solute permeation experiments, the feed solution was supplied from a magnetically stirred polyethylene reservoir to ensure continuous and consistent mixing. Feed solution temperature was maintained at 25±1° C. using a chiller (4100 R20 Isotemp; Thermo-Fisher Scientific, MA), which recirculated water through a shell and tube heat exchanger. For each membrane and solution combination, four transmembrane pressures (TMP) were selected within the range of 6.8 to 27.5 bar. Feed and permeate samples were collected every 30 min to determine the permeate flux (measured gravimetrically), acid concentrations (measured via HPLC), and solution pH. The permeate flux and solute rejection for each applied pressure are reported as the average of three measurements after the system reached steady state. Results obtained from the permeation experiments were analyzed using a solution-diffusion model.

Results from NF/RO Studies

Comparison of membrane performance. Among the five membranes evaluated in this study, the BW30XFR membrane demonstrated the highest acetic acid rejection (98.6%) at 27.5 bar. In general, similar rejection behavior was observed for the BW30XFR and NF90 membranes across the pressure range. Without intending to be bound by theory, this was attributed to the similar chemistries of the active layers in these TFC membranes; both BW30XFR and NF90 are composed of fully aromatic polyamide.

Each experimental data set was also modeled using a solution diffusion model to obtain a solute permeability coefficient, B, along with a water permeability coefficient, A. Since the water and solute permeability depend on the fundamental transport characteristics of the membrane materials, together, A and B largely define the selective layer performance of NF and RO membranes. Without intending to be bound by theory, an ideal membrane has both high water permeability (large A) and high selectivity (low B). However, it has been proposed that membranes exhibit a permeability-selectivity tradeoff, a phenomenon that limits the application of pressure-driven membranes. Greater water permeability is coupled with greater solute permeability, thus lower solute rejection. This phenomenon has been well documented for gas and liquid membrane separations (including desalination) by a wide range of NF and RO membranes. The results indicated that this tradeoff relationship extended to acetic acid when semi-aromatic and fully aromatic polyamide materials were used for membrane separation.

pH Effects. In order to understand the effects of pH on acetic acid separation, experiments were conducted with acetic acid solutions of 9 g/L (total acetic acid plus acetate concentration) across a range of pH values from 2.8 to 9.8. Permeate flux and rejection were measured at constant temperature for one NF membrane (DuPont NF) that contained a semi-aromatic polyamide active layer and one RO membrane (BW30XFR) that contained a fully aromatic polyamide active layer. Scanning electron microscopy confirmed that the chemical composition of the membranes was unaffected by the various pH conditions. As the pH of the feed solution increased, acetic acid rejection increased, corresponding to decreases in the permeate flux of each membrane. Without intending to be bound by theory, it is believed that this was likely attributed to increased electrostatic repulsion between the membrane surface and solute at high pH (i.e., 9.8). In particular, as the feed solution pH increased, it was expected that carboxylic groups deprotonated, leading to a negative surface charge that corresponds to greater acetate rejection.

Concentration effects. To understand the effects of acetic acid concentration on separation, the permeate flux and rejection were measured using different acetic acid concentrations (9 to 80 g/L, pH=6.3) for one NF membrane. The NF* membrane was chosen because of its combination of high permeate flux and acetate rejection. At 27 bar applied pressure, both permeate flux and acetic acid rejection decreased dramatically with increasing acetic acid concentration in feed solution. The permeate flux depended on the net driving pressure (i.e., difference between hydraulic and osmotic pressures), so without intending to be bound by theory, the decrease in permeate flux was attributed to the increase in osmotic pressure associated with increased solute concentration. Moreover, the decrease in permeate flux was believed to correspond to a decrease in solute rejection. Increasing the concentration by a factor of 8 (from 9 to 80 g/L) resulted in a 92% decrease in permeate flux and 62% decrease in solute rejection. These observations indicated that feed concentration can significantly affect membrane performance. The results demonstrated that in order to achieve a consistently high acetic acid rejection, a high permeate flux must also be maintained.

Evaluation of IX Resins and NF/RO Membranes as Separation Techniques

The performance of technologies evaluated in this study for acetic acid separation from 9 g/L acetic acid solution (pH=6.3) are summarized in Table 3, below.

TABLE 3

Evaluation of Acetic Acid Removal Technologies

| Technology | Test Material | Test Conditions | Separation ratio (% acetate removal) | Lowest concentration in effluent (g/L) |
|---|---|---|---|---|
| Strong-base IX resin | IRN-78 | 0-600 g wet resin/L solution | 13.1-95.1 | 0.44 |
| | A26 | | 10.1-93.1 | 0.60 |
| Weak-base IX resin | IRA-67 | | 1.9-15.3 | 7.69 |
| | WA10 | | 1.9-21.0 | 7.18 |
| | Dowex-66 | | 3.9-42.7 | 5.02 |
| NF | NF270 | 6.8-27.5 bar | 55.0-74.5 | 2.51 |
| | NF90 | | 92.8-97.6 | 0.24 |
| | NF* | | 60.1-83.1 | 1.73 |
| RO | BW30XFR | | 91.9-98.6 | 0.13 |
| | SE | | 82.5-95.4 | 0.42 |

In summary, this example demonstrates that each of IX resins and NF/RO membranes can be used to separate SCOAs from organic wastes.

What is claimed is:

1. A method of organic waste stream conversion comprising:
pretreating an anaerobic consortium selectively isolated from one or more of cheese, yogurt, saline soil, kefir, and probiotics with an acid shock treatment, a heat treatment, or a combination thereof to transform the anaerobic consortium into an acidogenic consortium and thereby form an inoculum;
admixing an organic waste stream with the inoculum; and
fermenting the organic waste stream with the inoculum using arrested methanogenesis performed with a sludge retention time of about 3 days to about 20 days and/or hydraulic retention time of no more than seven days at a pH of 7.5 or less to generate an organic product comprising one or more organic acids and/or alcohols.

2. The method of claim 1 wherein the fermenting is performed at a pH of 6.0 or less and/or the sludge retention time is no more than 7 days.

3. The method of claim 1, wherein the acid shock treatment comprises subjecting the anaerobic consortium to a pH of about 4 or less.

4. The method of claim 1, wherein the heat treatment comprises subjecting the anaerobic consortium to a temperature of at least 80° C.

5. The method of claim 1, wherein each of the acid shock treatment and/or the heat treatment is about 2 hours to about 15 hours.

6. The method of claim 1, wherein the fermenting is performed at a temperature of about 30° C. to about 70° C.

7. The method of claim 6, wherein the fermenting is performed at a temperature of about 30° C. to about 40° C., wherein the organic product comprises lactic acid and other organic acids comprising one or more of acetic acid, butyric acid, and propionic acid, wherein the lactic acid is present in an amount greater than the other organic acids.

8. The method of claim 6, wherein the fermenting is performed at a temperature of about 45° C. to about 70° C., wherein the organic product comprises butyric acid and acetic acid and other organic acids comprising one or more of formic acid and propionic acid, wherein the butyric acid and acetic acid are present in amounts greater than the other organic acids, and wherein the organic product comprises ethanol.

9. The method of claim 1, wherein the anaerobic consortium comprises one or more bacteria selected from the group consisting of Bacillaceae, Clostridiaceae, Lactobacillaceae, Streptococcaceae, Paenibacillaceae, and any combination thereof.

10. The method of claim 1, further comprising pretreating the organic waste stream to wash out methanogens from the anaerobic consortium.

11. The method of claim 10, wherein pretreating comprises aerating the organic waste stream with oxygen.

12. The method of claim 1, wherein the organic product comprises at least about 10 g/L lactic acid.

13. The method of claim 1, wherein the organic product comprises at least about 60 g/L lactic acid.

14. The method of claim 1, wherein the organic product comprises at least about 10 g/L butyric acid and acetic acid.

15. The method of claim 1, wherein the organic product comprises one or more of formic acid, acetic acid, propionic acid, butyric acid, isobutyric acid, valeric acid, isovaleric acid, and ethanol.

16. The method of claim 1, further comprising separating the one or more organic acids and/or alcohols from the organic product to provide an extracted product.

17. The method of claim 16, wherein the one or more organic acids and/or alcohols is separated from the organic product with an ion-exchange resin, adsorbents, membrane filtration, electrodialysis, electrodeionization or a combination thereof.

18. The method of claim 16, wherein the extracted product comprises from about 20 wt % to about 40 wt % lactic acid.

19. The method of claim 1, wherein the organic waste stream comprises cheese whey wastewater, brewery wastewater, food waste, industrial organic waste, organic fraction of municipal solid waste or a mixture thereof.

* * * * *